(12) United States Patent
Gerritsma et al.

(10) Patent No.: US 6,569,863 B1
(45) Date of Patent: May 27, 2003

(54) BICYCLIC HETEROAMATIC COMPOUNDS USEFUL AS LH AGONISTS

(75) Inventors: G. G. Gerritsma, Vezelstraat (NL); N. C. R. Van Straten, Leidsel (NL); A. E. P. Adang, Eindhoven (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/937,416

(22) PCT Filed: Apr. 3, 2000

(86) PCT No.: PCT/EP00/02865
§ 371 (c)(1),
(2), (4) Date: Sep. 26, 2001

(87) PCT Pub. No.: WO00/61586
PCT Pub. Date: Oct. 19, 2000

(30) Foreign Application Priority Data

Apr. 8, 1999 (EP) .............................. 99201152

(51) Int. Cl.[7] ..................... A61K 31/505; C07D 495/04
(52) U.S. Cl. .................................... 514/260.1; 544/278
(58) Field of Search ....................... 544/278; 514/260.1

(56) References Cited

FOREIGN PATENT DOCUMENTS

| WO | WO 93 13664 A | 7/1993 |
|----|---------------|--------|
| WO | WO 95 28405 A | 10/1995 |
| WO | WO 96 14319 A | 5/1996 |
| WO | WO 97 14697 A | 4/1997 |
| WO | WO 97 41126 A | 11/1997 |

OTHER PUBLICATIONS

Khalil et al., Chem. Abstract 115:92208, 1991.*
Briel, D.: "Synthese von Thieno–Heterocyclen ausgehend von substituierten 5–Methylthio–thiophen–4–carbonitrilen." Pharmazie, vol. 53, No. 4, 1998, pp. 227–231, Abstract.
Geies, A.A. et al.: "Syntheses of Thieno[2', 3':4,5]pyrimido [2,1–c] [1,2,4]triazoles and Pyrazolylthieno [2,3–d'] [4,5–d'] dipyrimidines." J. Chem. Synop, vol. 124, 1998, pp. 290–291.
Chemical Abstracts, vol. 125, No. 13, Sep. 23, 1996, Abstract No. 167905k, Tumkevicius, S.: "Synthesis of 3,4–dihydro–5H–1–thia–3,5,6,8–tetraazaacenaphthylenes." p. 1155, Khim. Geterotsikl Soedin, vol. 1, 1996, pp. 103–105, Abstract Only.

Tumkevicius, S.: "A Facile Synthesis of 5H–1–thia–3,5,6, 8–tetraazaacenaphthylenes." Liebigs. Ann, vol. 9, 1995, pp. 1703–1705.

Sayed A. et al., "Syntheses of Some Thieno['2,3–d]Pyrimidines" Sulfur Letters, vol. 9, No. 3, 1989, pp. 101–108.

* cited by examiner

Primary Examiner—Deepak Rao
(74) Attorney, Agent, or Firm—Mark W. Milstead

(57) ABSTRACT

The invention relates to a bicyclic heteroaromatic derivative compound according to general formula (I), or a pharmaceutically acceptable salt thereof, wherein $R^1$ is $NR^5R^6$, $OR^5$, $SR^5$ or $R^7$; $R^5$ and $R^6$ are independently selected from H, (1–8C)alkyl, (2–8C)alkenyl, (2–8C)alkynyl, (3–8C) cycloalkyl, (2–7C)heterocycloalkyl, alkyl(1–8C)carbonyl, (6–14C)arylcarbonyl, (6–14C)aryl or (4–13C)heteroaryl, or $R^5$ and $R^6$ together are joined in a (2–7C)heterocloalkyl ring; $R^7$ is (3–8C)cycloalkyl, (2–7C)heterocycloalkyl, (6–14C)aryl or (4–13C)heteroaryl, $R^2$ is (1–8C)alkyl, (2–8C)alkenyl, (2–8C)alkynyl, or (6–14C)aryl or (4–13C) heteroaryl, both optionally substituted with one or more substituents selected from (1–8C)alkyl, (1–8C)alkylthio, (1–8C)(di)alkylamino, (1–8C)alkoxy, (2–8C)alkenyl, or (2–8C)alkynyl; $R^3$ is (1–8C)alkyl, (2–8C)alkenyl, (2–8C) alkynyl, (3–8C)cycloalkyl, (2–7C)heterocycloalkyl, or (6–14C)aryl or (4–13C)heteroaryl, both optionally substituted with one or more substituents selected from (1–8C) alkyl, (1–8C)(di)alkylamino or (1–8C)alkoxy; X is S, O or $N(R^4)$; $R^4$ is H, (1–8C)alkyl, (1–8C)alkylcarbonyl, (6–14C) arylcarbonyl or (6–14C)aryl(1–8C)alkyl; Y is CH or N; Z is $NH_2$ or OH; A is S, N(H), $N(R^9)$, O or a bond; $R^9$ can be selected from the same groups as described for $R^2$ and B is N(H), O or a bond. The compounds of the invention have LH receptor activating activity and can be used in fertility regulating therapies.

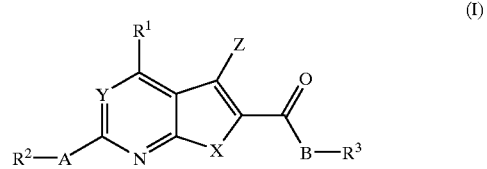

6 Claims, No Drawings

BICYCLIC HETEROAMATIC COMPOUNDS USEFUL AS LH AGONISTS

This application is a 371 of PCT/EP00/02865 filed Apr. 3, 2000.

The invention relates to compounds having glycoprotein hormone agonistic or antagonistic activity, in particular to compounds having Luteinizing Hormone (LH) agonistic activity. The invention furthermore relates to byciclic heteroaromatic derivative compounds, to pharmaceutical compositions containing the same as well as to the use of these compounds in medical therapy, particularly for use as a control of fertility.

Gonadotropins serve important functions in a variety of bodily functions including metabolism, temperature regulation and the reproductive process. The hypophyseal gonadotropin FSH for example plays a pivotal role in the stimulation of follicle development and maturation whereas LH induces ovulation (Sharp, R. M. Clin Endocrinol. 33:787–807, 1990; Dorrington and Armstrong, Recent Prog. Horm. Res. 35:301–342, 1979). Currently, LH is applied clinically, in combination with FSH, for ovarian stimulation i.e. ovarian hyperstimulation for in vitro fertilisation (IVF) and induction of ovulation in infertile anovulatory women (Insler, V., Int. J. Fertility 33:85–97, 1988, Navot and Rosenwak, J. Vitro Fert. Embryo Transfer 5:3–13, 1988), as well as for male hypogonadism and male infertility.

Gonadotropins act on specific gonadal cell types to initiate ovarian and testicular differentiation and steroidogenesis. The actions of these pituitary and placental hormones are mediated by specific plasma membrane receptors that are members of the large family of G-protein coupled receptors. They consist of a single polypeptide with seven transmembrane domains and are able to interact with the Gs protein, leading to the activation of adenyl cyclase.

Gonadotropins destined for therapeutic purposes can be isolated from human urine sources and are of low purity (Morse et al, Amer. J. Reprocud. Immunol. and Microbiology 17:143, 1988). Alternatively, they can be prepared as recombinant gonadotropins.

As with other therapeutic proteins, it is necessary to administer gonadotropins either subcutaneous or intramuscular. It would be advantageous, however, to activate the receptor with a small molecule that could be administered through e.g. the oral or transdermal route.

The present invention describes the preparation of such low molecular weight hormone analogs that selectively activate one of the gonadotropin receptors. This should be considered as one of the major advantages of the present invention.

Thus, the invention resides in bicyclic heteroaromatic derivatives according to general formula I, or a pharmaceutically acceptable salt thereof,

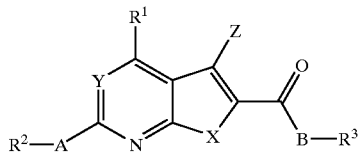

Formula I wherein
- $R^1$ is $NR^5R^6$, $OR^5$, $SR^5$ or $R^7$, preferably $R^1$ is $R^7$;
- $R^5$ and $R^6$ are independently selected from H, (1–8C)alkyl, (2–8C)alkenyl, (2–8C)alkynyl, (3–8C)cycloalkyl, (2–7C)heterocycloalkyl, (1–8C)alkylcarbonyl, (6–14C)arylcarbonyl, (6–14C)aryl or (4–13C)heteroaryl, or $R^5$ and $R^6$ together are joined in a (2–7C)heterocycloalkyl ring;
- $R^7$ is (3–8C)cycloalkyl, (2–7C)heterocycloalkyl, (6–14C)aryl or (4–13C)heteroaryl; preferably $R^7$ is (6–14C)aryl or (4–13C)heteroaryl;
- $R^2$ is (1–8C)alkyl, (2–8C)alkenyl, (2–8C)alkynyl, or (6–14C)aryl or (4–13C)heteroaryl, both optionally substituted with one or more substituents selected from (1–8C)alkyl, (1–8C)alkylthio, (1–8C)(di)alkylamino, (1–8C)alkoxy, (2–8C)alkenyl, or (2–8C)alkynyl;
- $R^3$ is (1–8C)alkyl, (2–8C)alkenyl, (2–8C)alkynyl, (3–8C)cycloalkyl, (2–7C)heterocycloalkyl, or (6–14C)aryl or (4–13C)heteroaryl, both optionally substituted with one or more substituents selected from (1–8C)alkyl, (1–8C)(di)alkylamino or (1–8C)alkoxy; preferably $R^3$ is (1–8C)alkyl, more preferably (1–4C)alkyl, even more preferably $R^3$ is isopropyl or tert-butyl;
- X is S, O or $NR^4$);
- $R^4$ is H, (1–8C)alkyl, (1–8C)alkylcarbonyl, (6–14C)arylcarbonyl or (6–14C)aryl(1–8C)alkyl;
- Y is CH or N, preferably Y is N;
- Z is $NH_2$ or OH;
- A is S, N(H), $N(R^9)$, O or a bond and
- $R^9$ can be selected from the same groups as described for $R^2$ and
- B is N(H), O, or a bond.

The alkyl group, alkenyl group or alkynyl group, if present in $R^5$ and/or $R^6$ in the above mentioned formula may optionally be substituted with one or more substituents selected from hydroxyl, (6–14C)aryl, (1–8C)alkoxy, (1–8C)alkylcarbonyloxy, (6–14C)arylcarbonyloxy, (1–8C)alkoxycarbonyl, (6–14C)aryloxycarbonyl, (1–8C)alkylcarbonyl, (6–14C)arylcarbonyl, amine, (1–8C)alkylaminocarbonyl, (6–14C)alkylaminocarbonyl, (1–8C)alkylcarbonylamino, (6–14C)arylcarbonylamino, (6–14C)(di)arylamino and/or (1–8C)(di)alkylamino.

If $R^7$ is (6–14C)aryl or (4–13C)heteroaryl, aryl may optionally be substituted at the ortho and/or meta position with one or more substituents selected from $R^8$, (6–14C)aryl, (4–13C)heteroaryl, (2–7C)heterocycloalkyl, (3–8C)cycloalkyl, $NHR^8$, $OR^8$ and/or $SR^8$ in which $R^8$ is (6–14C)aryl, (4–13C)heteroaryl, (1–8C)alkylcarbonyl, (6–14C)arylcarbonyl, (1–8C)alkyl, (2–8C)alkenyl, (2–8C)alkynyl, the alkyl group of which may be optionally substituted with one or more substituents selected from hydroxyl, (1–8C)alkoxy, (2–7C)heterocycloalkyl((1–8C)alk)oxy, (3–8C)cycloalkyl((1–8C)alk)oxy, (6–14C)aryl((1–8C)alk)oxy, (4–13C)heteroaryl((1–8C)alk)oxy, (2–7C)heterocycloalkyl, (3–8C)cycloalkyl, (6–14C)aryl, (4–13C)heteroaryl, (1–8C)alkoxycarbonyl, (6–14C)aryloxycarbonyl, (1–8C)alkylcarbonyloxy, (6–14C)arylcarbonyloxy, (1–8C)alkylcarbonyl, (6–14C)arylcarbonyl, amine, (1–8C)alkylaminocarbonyl, (6–14C)alkylaminocarbonyl, (1–8C)alkylcarbonylamino, (6–14C)arylcarbonylamino, (6–14C)(di)arylamino and/or (1–8C)(di)alkylamino. Preferably the substituents at aryl in $R^7$ are chosen from $NHR^8$ or $OR^8$. $R^8$ preferably is (1–8C)alkylcarbonyl, (6–14C)arylcarbonyl, (1–8C)alkyl. The most preferred substituents in the alkyl group are (2–7C)heterocycloalkyl, (1–6C)(di)alkylamino and amine.

The alkyl group, alkenyl group or alkynyl group, if present in $R^9$ or $R^2$ in the above mentioned formula may optionally be substituted with one or more substituents selected from (6–14C)aryl, (4–13C)heteroaryl, (1–8C)

alkylcarbonyl, (6–14C)arylcarbonyl, (1–8C) alkylcarbonyloxy, (6–14C)arylcarbonyloxy, (6–14C)aryloxycarbonyl and/or (1–8C)alkoxycarbonyl.

The alkyl group, alkenyl group or alkynyl group, if present in $R^3$ in the above mentioned formula may optionally be substituted with one or more substituents selected from hydroxyl, (1–8C)alkoxy, (6–14C)aryloxy, (3–8C)cycloalkyl((1–8C)alk)oxy, (2–7C)heterocycloalkyl((1–8C)alkoxy, (6–14C)aryl((1–8C)alkoxy, (4–13C)heteroaryl((1–8C)alk)oxy, (2–7C)heterocycloalkyl, (6–14C)aryl, (4–13C)heteroaryl, (1–8C)alkoxycarbonyl, (6–14C)aryloxycarbonyl(1–8C)alkylcarbonyloxy, (6–14C)arylcarbonyloxy, (1–8C)alkylcarbonyl, (6–14C)arylcarbonyl, amine, (1–8C)alkylaminocarbonyl, (6–14C)arylaminocarbonyl, (1–8C)alkylcarbonylamino, (6–14C)arylcarbonylamino, (6–14C)(di)arylamino or (1–8C)(di)alkylamino.

Preferred compounds according to the invention are compounds according to general formula I wherein X is S and/or Z is $NH_2$. Amongst these preferred compounds those wherein X is S and Z is $NH_2$ are especially preferred, even more preferred are those compounds wherein in addition Y is N. Most preferred are the compounds which in addition to the above mentioned definitions of X, Z and Y are defined by $R^1$ being (6–14C)aryl or (4–13C)heteroaryl. Most preferably A is S.

Highly preferred compounds of the invention are the bicyclic heteroaromatic derivative compounds having the general formula I wherein $R^1$ is (6–14C)aryl or (4–13C)heteroaryl, $R^2$ is (1–8C)alkyl, (2–8C)alkenyl, (2–8C)alkynyl, or (6–14C)aryl or (4–13C)heteroaryl, both optionally substituted with one or more substituents selected from (1–8C)alkyl, (1–8C)alkylthio, (1–8C)alkoxy, (2–8C)alkenyl, or (2–8C)alkynyl, $R^3$ is (1–8C)alkyl, (2–8C)alkenyl, (2–8C)alkynyl, (3–8C)cycloalkyl, (2–7C)heterocycloalkyl, or (6–14C)aryl or (4–13C)heteroaryl, both optionally substituted with one or more substituents selected from (1–8C)alkyl, (1–8C)(di)alkylamino or (1–8C)alkoxy X is S, Z is $NH_2$, A is S and B is N(H), O, or a bond.

These compounds have the general structure:

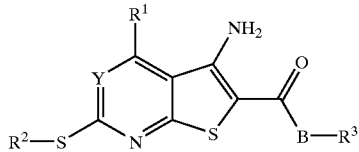

Formula II wherein $R^1$, $R^2$, $R^3$ and B have the above mentioned definitions including the substitutions at the alkyl, alkenyl, alkynyl, aryl or heteroaryl groups in $R^2$, $R^3$. The substitutions of the aryl or heteroaryl groups in $R^1$ are defined previously for $R^7$.

The most preferred compounds are the compounds of general formula I, more preferably formula II, wherein B is N or O, B is N being the most preferred. $R^2$ and/or $R^3$ preferably are (1–8C)alkyl, more preferably (1–4C)alkyl and Y preferably is N.

Particularly preferred compounds according to the invention are those wherein $R^3$ is isopropyl or tert-butyl, tert-butyl being the most preferred.

Excluded from the invention are the compounds ethyl 5-amino-4-phenyl-2-ethoxycarbonylmethylthio-thieno[2,3-d]pyrimidine-6-carboxylate, methyl 5-amino-4-phenyl-2-methylthio-thieno[2,3-d]pyrimidine-6-carboxylate, ethyl 5-amino-4-phenyl-2-methylthio-thieno[2,3-d]pyrimidine-6-carboxylate, 6-acetyl-5-amino-4-phenyl-2-(2-oxopropylthio)-thieno[2,3-d]pyrimdine, 5-amino-6-benzoyl-4-phenyl-2-phenylcarbonylmethylthio-thieno[2,3-d]pyrimidine or 5-amino-6-(4-chlorobenzoyl)-4-phenyl-2-[(4-chlorophenyl)carbonylmethylthio]-thieno[2,3-d]pyrimidine.

The disclaimer relates to the disclosures in Phosph. Sulf. Sil. Rel. Chem: 60, 223–231, 1991; J. Chem. Res., Synop. (6):290–291, 1998 and Suflir Lett. 9:101–108, 1989.

The term (1–8C)alkyl as used in the definition of formulas I an II means a branched or unbranched alkyl group having 1–8 carbon atoms, for example methyl, ethyl, propyl, isopropyl, butyl, sec-butyl, tert-butyl, hexyl and octyl. (1–6C)Alkyl groups are preferred, (1–3C)alkyl being the most preferred.

The term (2–8C)alkenyl means a branched or unbranched alkenyl group having 2–8 carbon atoms, such as ethenyl, 2-butenyl etc.

The term (2–8C)alkynyl means a branched or unbranched alkynyl group having 2–8 carbon atoms, such as ethynyl and propynyl.

The term (3–8C)cycloalkyl means a cycloalkyl group having 3–8 carbon atoms, being cyclopropyl, cyclobutyl, cyclopentyl, cyclohexyl, cycloheptyl or cyclo-octyl.

The term (2–7C)heterocycloalkyl means a heterocycloalkyl group having 3–8 carbon atoms, preferably 3–5 carbon atoms, and at least including one heteroatom selected from N, O or S. Preferred are N or O. Most preferred are piperidine, morpholine and pyrrolidine.

The term (1–8C)alkoxy means an alkoxy group having 1–8 carbon atoms, the alkyl moiety having the same meaning as previously defined. (1–6C)Alkoxy groups are preferred, (1–3C)alkoxy being the most preferred.

The term (1–8C)alkoxycarbonyl means an alkoxycarbonyl group, the alkyl group of which contains 1–8 carbon atoms and has the same meaning as previously defined.

The term (1–8C)(di)alkylamino means an (di)alkylamino group having 1–8 carbon atoms, the alkyl moiety having the same meaning as previously defined.

The term (6–14C)(di)arylamino means an (di)arylamino group having 6–14C carbon atoms, the aryl moiety having the same meaning as previously defined.

The term (1–8C)alkylthio means an alkylthio group having 1–8 carbon atoms, the alkyl moiety having the same meaning as previously defined.

The term (6–14C)aryl means an aromatic hydrocarbon group having 6–14 carbon atoms, such as phenyl, naphthyl, tetrahydronaphthyl, indenyl, anthracyl, which may optionally be substituted with one or more substituents such as—but not limited to—hydroxy, halogen, nitro, trifluoromethyl, cyano, (1–8C)alkylcarbonylamino, (1–8C)alkylamninocarbonyl or (1–8C)(di)alkylamino, the alkyl moieties having the same meaning as previously defined. The preferred aromatic hydrocarbon group is phenyl.

The term (6–14C)aryloxycarbonyl means an aryloxycarbonyl group, the aryl group of which contains 6–14 carbon atoms and has the same meaning as previously defined.

The term (6–14C)aryl(1–8C)alkyl means an arylalkyl group having 7–22 carbon atoms, wherein the alkyl group is a (1–8C)alkyl group and the aryl group is a (6–14C)aryl as previously defined. Phenyl(1–8C)alkyl groups are preferred arylalkyl groups, such as benzyl.

The term (4–13C)heteroaryl means a substituted or unsubstituted aromatic group having 3–13 carbon atoms, preferably 4–9, at least including one heteroatom selected from N, O and/or S, like imidazolyl, thienyl, benzthienyl, quinolyl, tetrahydroquinolyl, isoquinolyl, tetrahydroisoquinolyl, indolyl, acridinolyl, furyl or pyridyl. The substituents on the heteroaryl group may be selected from the group of substituents listed for the aryl group. Preferred heteroaryl groups are thienyl, furyl and pyridyl.

The term joined in a (2–7C)heterocycloalkyl ring in the definition of $NR^5R^6$, where $R^5$ and $R^6$ together with the nitrogen atom to which they are bonded are a ring, means a ring containing the nitrogen atom and further having at most 2–7 carbon atoms, which ring may contain unsaturated bonds or one or more heteroatoms selected from N, O and/or S. Examples of such rings are azetidine, pyrrolidine, piperidine, piperazine, morpholine and thiomorpholine.

The term halogen means fluorine, chlorine, bromine or iodine.

The term (2–7C)heterocycloalkyl(1–8C)alkoxy means a heterocycloalkyl group containing 3–8 carbon atoms as defined previously, attached to a (1–8C)alkoxy group, the alkoxy moiety having the meaning as previously defined.

The term (3–8C)cycloalkyl(1–8C)alkoxy means a cycloalkyl group containing 3–8 carbon atoms as defined previously, attached to a (1–8C)alkoxy group, the alkoxy moiety having the meaning as previously defined.

The term (6–14C)aryl(1–8C)alkoxy means an aryl group containing 6–14 carbon atoms as defined previously, attached to a (1–8C)alkoxy group, the alkoxy moiety having the meaning as previously defined. (4–13C) Heteroarylalkoxy groups are analogs of the (6–14C) arylalkoxy groups, at least including one heteroatom selected from N, O and S.

The term (1–8C)alkylcarbonyl means an alkylcarbonyl group, the alkyl group of which contains 1–8 carbon atoms and has the same meaning as previously defined.

The term (6–14C)arylcarbonyl means an arylcarbonyl group, the aryl group of which contains 6–14 carbon atoms and has the same meaning as previously defined.

The term (1–8C)alkylcarbonyloxy means an alkylcarbonyloxy group, the alkyl group of which contains 1–8 carbon atoms and has the same meaning as previously defined.

The term (6–14C)arylcarbonyloxy means an arylcarbonyloxy group, the aryl group of which contains 6–14 carbon atoms and has the same meaning as previously defined.

The term (1–8C)alkylaminocarbonyl means an alkylaminocarbonyl group, the alkyl group of which contains 1–8 carbon atoms and has the same meaning as previously defined.

The term (6–14C)arylaminocarbonyl means an arylaminocarbonyl group, the aryl group of which contains 6–14 carbon atoms and has the same meaning as previously defined.

The term (1–8C)alkylcarbonylamino means an alkylcarbonylamino group, the alkyl group of which contains 1–8 carbon atoms and has the same meaning as previously defined.

The term (6–14C)arylcarbonylamino means an arylcarbonylamino group, the aryl group of which contains 6–14 carbon atoms and has the same meaning as previously defined.

The term (2–7C)heterocycloalkyloxy means a heterocycloalkyl group containing 3–8 carbon atoms as defined previously, attached to an oxygen atom.

The term (3–8C)cycloalkyloxy means a cycloalkyl group containing 3–8 carbon atoms as defined previously, attached to an oxygen atom.

The term (6–14C)aryloxy means an aryl group containing 6–14 carbon atoms as defined previously, attached to an oxygen atom. (4–13C)Heteroaryloxy groups are analogs of the (6–14C)aryloxy groups, at least including one heteroatom selected from N, O and S.

It has been shown that compounds of the above mentioned formula I are capable of binding to the LH recepotor and show agonistic LH activity.

The invention further resides in a pharmaceutical composition comprising a bicyclic heteroaromatic derivative compound or salts thereof having the general formula I.

Pharmaceutical compositions which comprise ethyl 5-amino-4-phenyl-2-ethoxycarbonylmethylthio-thieno[2,3-d]pyrimidine-6-carboxylate, methyl 5-amino-4-phenyl-2-methylthio-thieno[2,3-d]pyrimidine-6-carboxylate or ethyl 5-amino-4-phenyl-2-methylthio-thieno[2,3-d]pyrimidine-6-carboxylate are within the ambit of the present invention. Thus, the compounds according to the invention can be used in therapy. A further aspect of the invention resides in the use of a bicyclic heteroaromatic compound having the general formula I for the manufacture of a medicament for the control of fertility. Preferably the present compounds are used to activate the LH receptor.

The bicyclic heteroaromatic derivative compounds of this invention may possess one or more chiral carbon atoms. The compounds may therefore be obtained as chirally pure compounds or as a mixture of diastereomers and/or enantiomers. Methods for obtaining the chirally pure compounds are well known in the art, e.g. crystallization or chromatography.

For therapeutic use, salts of the compounds of formula I are those wherein the counterion is pharmaceutically acceptable. However, acid addition salts of bases according to formula I, may also find use, for example, in the preparation or purification of a pharmaceutically acceptable compound. All salts, whether pharmaceutically acceptable or not, are included within the ambit of the present invention.

Examples of acid addition salts include those derived from mineral acids such as hydrochloric acid, phosphoric acid, sulphuric acid, preferably hydrochloric acid and organic acids like citric acid, tartaric acid, acetic acid, lactic acid, maleic acid, malonic acid, fumaric acid, glycolic acid, succinic acid, and the like.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient In case of in vitro or ex vivo applications, like in IVF applications, the compounds of the inventions are to be used in the incubation media in a concentration of approximately 0.01–5 μg/ml.

The present invention thus also relates to pharmaceutical compositions comprising a bicyclic heteroaromatic compound according to formula I, i.e. including pharmaceutical compositions comprising ethyl 5-amino-4-phenyl-2-ethoxycarbonylmethylthio-thieno[2,3-d]pyrimdine-6-carboxylate, methyl 5-amino-4-phenyl-2-methylthio-thieno [2,3-d]pyrimidine-6-carboxylate or ethyl 5-amino-4-phenyl-2-methylthio-thieno[2,3-d]pyrimidine-6-carboxylate, 6-acetyl-5-amino-4-phenyl-2-(2-oxopropylthio)-thieno[2,3-d]pyrimidine, 5-amino-6-benzoyl-4-phenyl-2-phenylcarbonylmethylthio-thieno[2,3-d]pyrimidine or 5-amino-4-chlorobenzoyl)-4-phenyl-2-[(4-chlorophenyl) carbonylmethylthio]-thieno[2,3-d]pyrimidine in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurized aerosols, nebulisers or insufflators.

The bicyclic heteroaromatic derivative compounds of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303, 306 (AKZO N.V.).

Thus, the compounds according to the present invention can be used for the same clinical purposes as the native LH, with the advantage that they display altered stability properties and can be administered differently.

The compounds of the present invention wherein B=NH, represented by formula (I-a) can generally be prepared following art-known condensation of an acid of formula (III) with an amine of formula (IV).

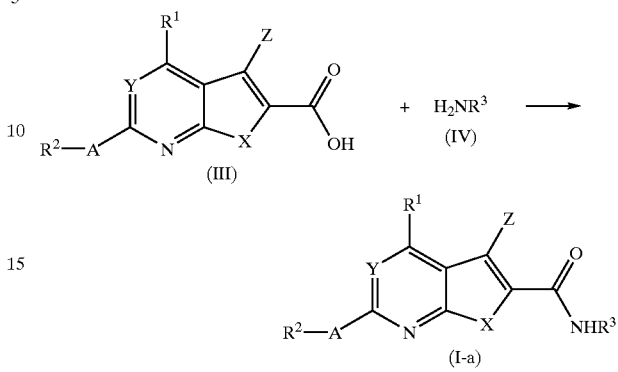

The above reaction is typically conducted at room temperature in a suitable solvent, e.g. an aprotic solvent such as N,N-dimethylformamide or dichloromethane, using a coupling reagent such as O-(benzotriazol-1-yl)-N,N,N',N'-tetramethyluronium tetrafluoroborate (TBTU) or bromotripyrrolidinophosphonium hexafluorophosphate (PyBrOP) and a tertiary base, e.g. N,N-diisopropylethylamine.

Likewise, compounds of formula (I) wherein B=O, being represented by formula (I-b) can be prepared in the same way as described above for compounds of formula (I-a), starting from acids with the general structure (III) and alcohols of formula (V).

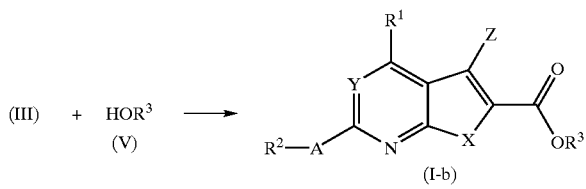

The compounds of formula (I) wherein B is a bond, represented by formula (I-c) can be prepared by condensation of pyridyl chlorides (VI) wherein W=GN or C(O)(OEt) with compounds of general structure (VII) in suitable solvents such as ethanol, methanol or tetrahydrofuran at elevated temperature (50° C.) in the presence of a base, e.g. sodium ethoxide, sodium methoxide, potassium carbonate or potassium hydroxide.

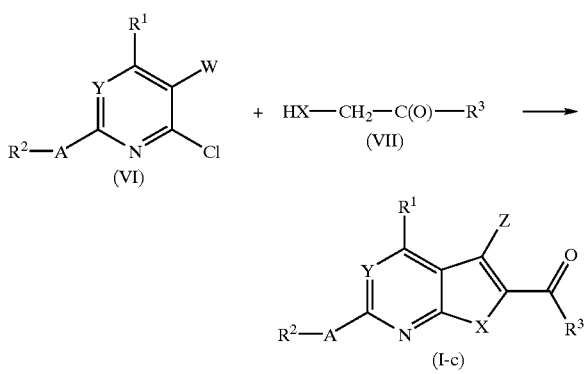

Alternatively, compounds of formula (I-c) wherein X=S, represented by formula (I-d) can also be prepared from thioamides of structure (VIII) wherein W is as previously defined, and compounds of formula (IX) wherein V=halogen such as bromide or chloride, via the abovementioned procedure.

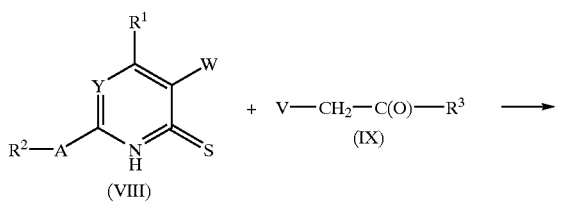

(VIII)   (IX)

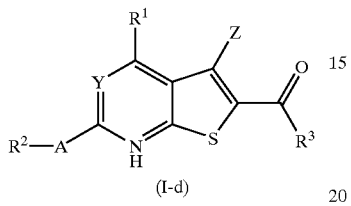

(I-d)

Related cyclizations are described in literature, see for example Y. A. Sharanin, A. M. Shestopalov and V. K. Promonenkov, J. Org. Chem. USSR (Engl. Transl), 20:1828 1984; Z. H. Klhalil and A. A. Geies, Phosph. Sulf. Silic. Relat. Elem. 60:223, 1991.

A suitable method for the preparation of intermediate acids (III) is the art-known base-mediated saponification of ethyl esters of general structure (X). Saponification takes place in the presence of a base such as lithium hydroxide, potassium hydroxide or sodium hydroxide in a mixture of aqueous dioxane at elevated temperature (80° C. to reflux).

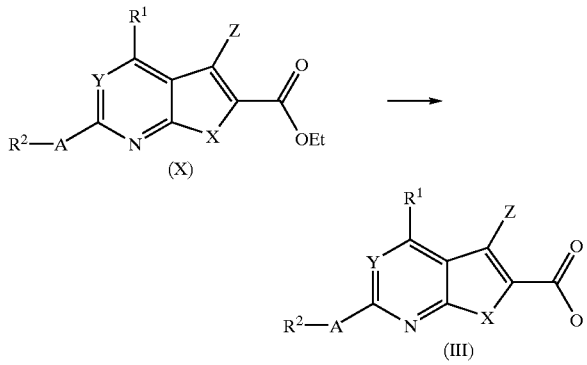

(X)

(III)

Compounds of formula (X) may be prepared by cyclization of pyridyl chlorides (VI) with HXCH$_2$C(O)OEt as described previously for the synthesis of compounds (I-c). In certain instances, an intermediate—not cyclized—product can be isolated, which cyclizes upon repeated treatment with base. Alternatively, compounds of formula (X) wherein X=S may also be prepared via the same procedure described for the synthesis of derivatives (I-d), by cyclization of (VIII) with VCH$_2$C(O)OEt (IX) wherein V is as previously defined.

Related cyclizations are found in literature. For example, thieno cyclizations are described by A. A. Santilli, D. H. Kim and S. V. Wanser, J. Heterocycl. Chem. 8:445, 1971; S. Kohra, Y. Tominaga and A. Hosomi, J. Heterocycl. Chem. 25:959, 1988; H. Vieweg, U. Krasselt, N. Bohm, J. Prantz and G. Wagner, Pharmazie 45:731, 1990; H. Vieweg and G. Wagner, Pharmazie 46:51, 1991; G. Wagner, H. Vieweg and S. Leitner, Pharmazie 48:588, 1993. Pyrrolo cyclizations are described e.g. by D. H. Kim and A. A. Santilli, J. Heterocycl. Chem. 6:819, 1969.

Compounds of formula (VI) wherein W is as previously defined, can be synthesized following literature procedures as described for example by A. A. Santilli D. H. Kim and S. V. Wanser, J. Heterocycl. Chem. 8:445, 1971. In a typical experiment, an amide of general structure (XI) is treated with POCl$_3$ at elevated temperature (80° C. to reflux). The addition of an appropriate solvent, e.g. dioxane, and/or the addition of either PCl$_5$ or N,N-dimethylaniline to the reaction mixture may result in shorter reaction times and higher yields of chlorides (VI).

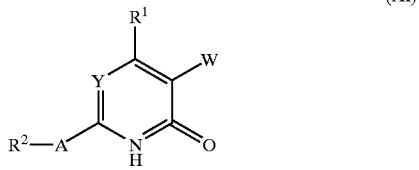

(XI)

In another approach, amides (XI) may be treated at elevated temperature (preferably reflux) with SOCl$_2$ to give compounds of formula (VI), as was described in literature by D. H. Kim and A. A. Santilli, J. Heterocycl. Chem. 6:819, 1969.

Compounds of formula (VIII) wherein W is as previously defined can be prepared by treatment of derivatives (XI) with a sulfurizing agent, e.g. P$_2$S$_5$ or Lawesson's Reagent in an appropriate solvent such as pyridine at elevated temperature (preferably reflux), see Z. H. Khalil, Phosph. Sulf. Silic. Relat. Elem. 60: 223, 1991.

Furthermore, compounds of general formula (VIII) wherein Y=CH and A is a bond, represented by formula (VIII-a) can be synthesized by cyclization of α,β-unsaturated ketones of formula (XII) and thioacetamide (XIII).

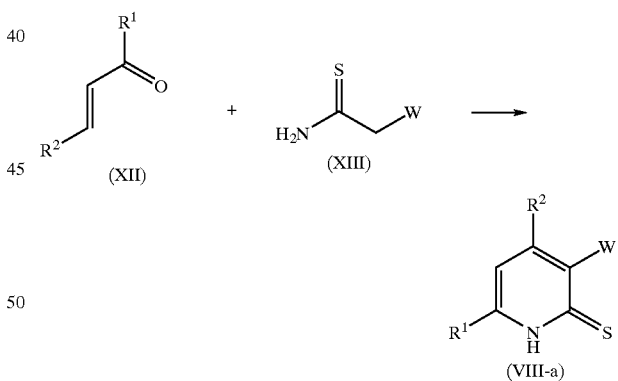

(XII)   (XIII)

(VIII-a)

In a typical experiment compounds (XII) and (XIII) are reacted in a solvent such as ethanol, methanol or tetrahydrofuran at elevated temperature (preferably reflux) in the presence of base, e.g. piperidine, triethylamine, sodium methoxide or sodium ethoxide. Related cyclizations are found in literature: H. Vieweg, V. Hanfeld, S. Leitner and G. Wagner, Pharmazie 44:639, 1989; H. Vieweg and G. Wagner. Pharmazie 46:51, 1991.

Alternatively, compounds of formula (VIII-a, W=CN) can be synthesized starting from α,β-unsaturated dinitriles of general structure (XIV) and thioacetamides (XV) as was described by G. A. H. Elgemeie, Heterocycles 31:123, 1990.

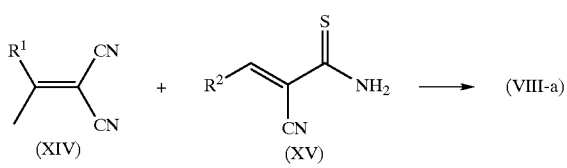

Compounds of formula (XI) wherein Y=N, represented by formula (XI-a) can be prepared via several literature-based approaches.

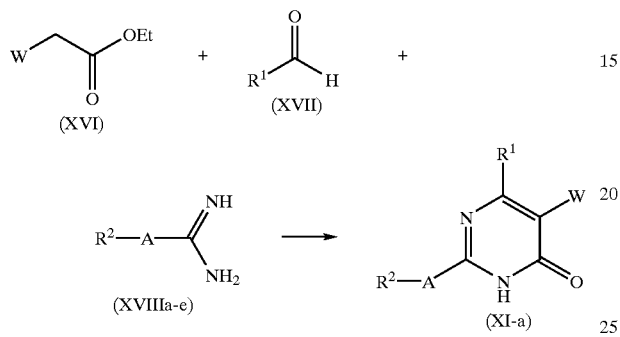

For example, derivatives of formula (XI-a) wherein R¹= (6–14C)aryl or (4–13C)heteroaryl may be synthesized by condensation of ethyl esters (XVI, wherein W is as previously defined), with aldehydes (XVII) and compounds (XVIII), which may be isothiourea (XVIII-a), isourea (XVIII-b), monosubstituted guanidines (XVII-c), disubstituted guanidines (XVIII-d) or amidines (XVIII-e).

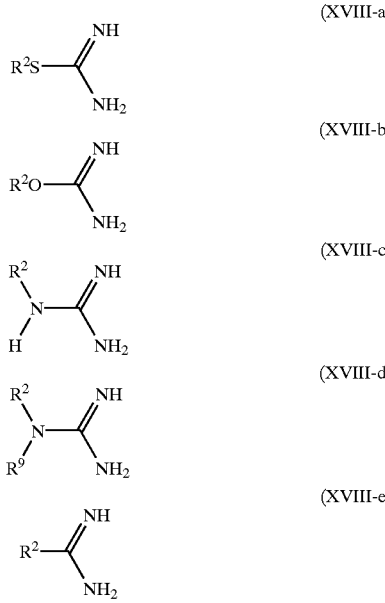

In a typical experiment, components (XVI), (XVII) and (XVIIIa–e) are suspended in an appropriate solvent, e.g. ethanol, methanol, N,N-dimethylformamide, N-methylpyrrolidinone, tetrahydrofuran or pyridine and a base such as potassium carbonate, sodium acetate, sodium methoxide or sodium ethoxide is added. Reaction takes place at elevated temperature (70° C. to reflux). After filtration, residues are taken up in water and acidified (pH 2) after which products (XI-a) precipitate (S. Kambe, K. Saito and H. Kishi, Synthesis 287 (1979); A. M. Abd-Elfattah, S. M. Hussain and A. M. El-Reedy, Tetrahedron 39, 3197 (1983); S. M. Hussain, A. A. El-Barbary and S. A. Mansour, J. Heterocycl. Chem. 22, 169 (1985)). In the case of W=C(O)OEt, aromatization occurs on the addition of an oxidant, such as DDQ or oxygen. Related cyclizations may also be performed on a solid support such as Merrifield resin using an appropriate linker, see for example A. L. Mrzinzik and E. R. Felder, J. Org. Chem. 63, 723 (1998); T. Masquelin, D. Sprenger, R. Baer, F. Gerber and Y. Mercadal, Helv. Chim. Acta 81, 646 (1998).

Alternatively, derivatives of formula (XI-a) wherein R¹ is not (6–14C)aryl or (4–13C)heteroaryl, may be prepared via substitution of Cl in derivatives of formula (VI-a) or substitution of 4-SMe in compounds of formula (XI-b).

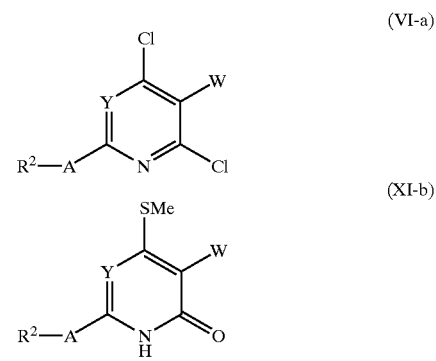

Related substitution reactions are found in literature, e.g. S. Kohra, Y. Tominaga and A. Hosomi, J. Heterocycl. Chem. 25:959, 1988; A. A. Santilli, D. H. Kim and S. V. Wanser, J. Heterocycl. Chem. 8:445, 1971; J. Clark, M. S. Shannet, D. Korakas and G. Varvounis, J. Heterocycl. Chem. 30:1065, 1993; S. Tumkevicius, Liebigs Ann. Org. Bioorg. Chem. 9:1703, 1995.

Pyridines of general formula (XI) wherein Y=CH, A=S and W=CN, represented by formula (XX) are accessible by sequential alkylation of α,β-unsaturated dinitriles of general structure (XIV) with carbon disulfide and alkyl iodide R²-I to give compounds of general formula (XIX), as described by P. Milart, Tetrahedron 54: 15643–15656, 1998. Cyclization of compounds of formula (XIX) under acidic conditions as described by K. Peseke, Z. Chem. 29:442443 (1989) yields pyridines of general formula (XX).

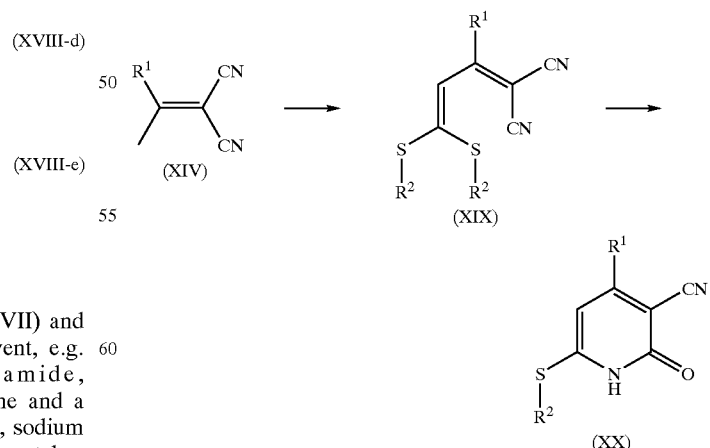

Methods to determine receptor binding as well as in vitro and in vivo assays to determine biological activity of gonadotropins are well known. In general, expressed receptor is contacted with the compound to be tested and binding or stimulation or inhibition of a functional response is measured.

To measure a functional response isolated DNA encoding the LH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759–776, 1991.

Methods to construct recombinant LH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then are then contacted with the test compound to observe binding, or stimulation or inhibition of a functional response.

Alternatively isolated cell membranes containing the expressed receptor may be used to measure binding of compound.

For measurement of binding radioactively or fluorescently labeled compounds may be used. As reference compound human recombinant LH can be used. In the alternative also competition binding assays can be performed.

Another assay involves screening for LH receptor agonist compounds by determining stimulation of receptor mediated cAMP accumulation. Thus, such a method involves expession of the receptor on the cell surface of a host cell and exposing the cell to the test compound. The amount of cAMP is then measured. The level of cAMP will be reduced or increased, depending on the inhibitory or stimulating effect of the test compound upon binding to the receptor.

In addition to direct measurement of e.g. cAMP levels in the exposed cell, cells lines can be used which in addition to transfection with receptor encoding DNA are also trarsfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch, Himmler, A and Czemilofsky, A. P. (1995) Curr.Opin-.Biotechnol. 6:574.

For selecting active compounds testing at $10^{-5}$ M must result in an activity of more than 20% of the maximal activity when LH is used as a reference. Another criterion might be the $EC_{50}$ value which must be $<10^{-5}$ M, preferably $<10^{-7}$ M.

The skilled artisan will recognize that desirable $EC_{50}$ values are dependent on the compound tested. For example, a compound with an $EC_{50}$ which is less than $10^{-5}$ M is generally considered a candidate for drug selection. Preferably this value is lower than $10^{-7}$ M. However, a compound which has a higher $EC_{50}$, but is selective for the particular receptor, may be even a better candidate.

Screening for LH receptor agonistic compounds can also be performed by using a mouse Leydig cell bioassay (Van Damme, M., Robersen, D. and Diczfalusy, E. (1974). Acta Endocrinol. 77:655–671 Mannaerts, B., Kloosterboer, H. and Schuurs, A. (1987). Neuroendocrinology of reproduction. R. Rolland et al. Eds., Elsevier Science Publishers B.V., 49–58). In this assay, stimulation of LH receptor mediated testosterone production can be measured in Leydig cells isolated from male mice.

To measure in vivo activity of LH receptor agonistic compounds ovulation induction in immature mice can be studied. In this assay immature female mice can be primed with urinary FSH and approximately 48 hours later treated with a LH agonistic compound. The animals are killed after LH agonist treatment and the number of ova in the oviduct can be microscopically assessed.

The compounds of the present invention can be applied clinically in those regimens where now LH or hCG is used. These include LH substitution among subjects with hypogonadal hypogonadism either male or female, midcycle administration to induce ovulation (ovulation induction (OI) or controlled hyperstimulation (COH) or stimulation of the corpus luteum.

The following examples are illustrative for the invention and should in no way be interpreted as limiting the scope of the invention.

EXAMPLES

Example 1

Ethyl 5-Amino-4-(3-methoxyphenyl)-2-methylthio-thieno[2,3-d]pyrimidine-6-carboxylate (a). 5-Cyano-4-(3-methoxyphenyl)-2-methylthio-6-oxopyrimidine A mixture of S-methylisothiourea sulfate (139 mg), 3-methoxybenzaldehyde (243 μl), ethyl cyanoacetate (112 μl) and potassium carbonate (145 mg) in abs. ethanol (2 ml) was stirred at 60° C. for 5 h. The reaction mixture was cooled to 0° C. in an ice bath, filtered and the residue was heated in water until a clear solution was obtained. The solution was acidified with 2N HCl to pH 2 and cooled to 0° C. in an ice bath. The resulting crystals were filtered off and dried in vacuo.

Yield: 186 mg. MS-ESI: $[M+H]^+=274.2$. TLC: Rf=0.50, silica gel, dichloromethane/methanol=9/1 v/v.

(b). 6-Chloro-5-cyano-4-(3-methoxphenyl)-2-methylthiopyridine $POCl_3$ (0.75 ml) was added to a stirred solution of 5-cyano-4-(3-methoxyphenyl)-2-methylthio-6-oxopyrimidine (305 mg) in dry dioxane (1 ml). After 3 h at 80° C., the mixture was cooled to 0° C. in an ice bath and crushed ice was slowly added. After cessation of the exothermic reaction, water was added (3 ml), the solids were filtered off and dried in vacuo.

Yield: 244 mg. MS-ESI: $[M+H]^+=292.2$. TLC: Rf=0.86, silica gel, dichloromethane.

(c). Ethyl 5-Amino-4-(3-methoxyphenyl)-2-methylthio-thieno[2,3-d]pyrimidine-6-carboxylate Sodium ethoxide (1.4N, 957 μl) was added to a stirred solution of ethyl 2-mercaptoacetate (92 μl) and 6-chloro-5- cyano-4-(3-methoxyphenyl)-2-methylthiopyrimidine (244 mg) in dry ethanol (4 ml). After 3 h at 50° C. the mixture was cooled to 0° C. in an ice bath, diluted with water (5 ml) and the solids were collected by filtration and dried in vacuo.

Yield: 260 mg MS-ESI: [M+H]$^+$=376.2. TLC: Rf=0.44, silica gel, dichloromethane.

Example 2

Ethyl 5-Amino-2-ethylthio-4-phenyl-thieno[2,3-d]pyrimidine-6-carboxylate

Cyclization of S-ethylisothiourea.HBr (185 mg), benzaldehyde (203 μl) and ethyl cyanoacetate (117 μl), treatment of the product with POCl$_3$ and subsequent reaction with ethyl 2-mercaptoacetate were performed according to the methods described in example 1.

Yield: 49 mg. MS-ESI: [M+H]$^+$=360.2. TLC: Rf=0.46, silica gel, dichloromethane.

Example 3

Ethyl 5-Amino-2-n-pentylthio-4-phenyl-thieno[2,3-d]pyrimidine-6-carboxylate

Cyclization of S-n-pentylisothiourea (146 mg), benzaldehyde (203 μl) and ethyl cyanoacetate (112 μl), treatment of the product with POCl$_3$ and subsequent reaction with ethyl 2-mercaptoacetate were performed according to the methods described in example 1.

Yield: 45 mg. MS-ESI: [M+H]$^+$=402.4. TLC: Rf=0.57, silica gel, dichloromethane.

Example 4

Ethyl 5-Amino-2-n-pentylthio-4-(3-thienyl)-thieno[2,3-d]pyrimidine-6-carboxylate Cyclization of S-n-pentylisothiouea (146 mg), thiophene-3-carboxaldehyde (183 μl) and ethyl cyanoacetate (112 μl), treatment of the product with POCl$_3$ and subsequent reaction with ethyl 2-mercaptoacetate were performed according to the methods described in example 1.

Yield: 4 mg. MS-ESI: [M+H]$^+$=408.2. TLC: $R_f$=0.65, silica gel, dichloromethane.

Example 5

Ethyl 5-Amino-4-(3-furyl)-2-n-pentylthio-thieno[2,3-d]pyrimidine-6-carboxylate

Cyclization of S-n-pentylisothiourea (146 mg), 3-furaldehyde (129 μl) and ethyl cyanoacetate (112 μl), treatment of the product with POCl$_3$ and subsequent reaction with ethyl 2-mercaptoacetate were performed according to the methods described in example 1.

Yield: 18 mg. MS-ESI: [M+H]$^+$=392.2. TLC: $R_f$=0.60, silica gel, dichloromethane.

Example 6

Ethyl 5-Amino-2-benzylthio-4-phenyl-thieno[2,3-d]pyrimidine-6-carboxylate

Cyclization of S-benzylisothiourea (203 mg), benzaldehyde (203 μl) and ethyl cyanoacetate (112 μl), treatment of the product with POCl$_3$ and subsequent reaction with ethyl 2-mercaptoacetate were performed according to the methods described in example 1.

Yield: 114 mg. MS-ESI: [M+H]$^+$=422.0. TLC: $R_f$=0.70, silica gel, dichloromethane.

Example 7

Ethyl 5-Amino-2-benzylthio-4-(3-thienyl)-thieno[2,3-d]pyrimidine-6-carboxylate

Cyclization of S-benzylisothiourea (203 mg), thiophene-3-carboxaldehyde (183 μl) and ethyl cyanoacetate (112 μl), treatment of the product with POCl$_3$ and subsequent reaction with ethyl 2-mercaptoacetate were performed according to the methods described in example 1.

Yield: 34 mg. MS-ESI: [M+H]$^+$=428.3. TLC: $R_f$=0.65, silica gel, dichloromethane.

Example 8

Ethyl 5-Amino-2-benzylthio-4-(3-furyl)-thieno[2,3-d]pyrimidine-6-carboxylate

Cyclization of S-benzylisothiourea (203 mg), 3-furaldehyde (129 μl) and ethyl cyanoacetate (112 μl), treatment of the product with POCl$_3$ and subsequent reaction with ethyl 2-mercaptoacetate were performed according to the methods described in example 1.

Yield: 38 mg. MS-ESI: [M+H]$^+$=412.2. TLC: $R_f$=0.60, silica gel, dichloromethane.

Example 9

Ethyl 5-Amino-2-benzylthio-4-(3-methoxyphenyl)-thieno[2,3-d]pyrimidine-6-carboxylate Cyclization of S-benzylisothiourea (203 mg), 3-methoxybenzaldehyde (243 μl) and ethyl cyanoacetate (112 μl), treatment of the product with POCl$_3$ and subsequent reaction with ethyl 2-mercaptoacetate were performed according to the methods described in example 1.

Yield: 31 mg. MS-ESI: [M+H]$^+$=452.2. TLC: $R_f$=0.52, silica gel, dichloromethane.

Example 10

Ethyl 5-Amino-2-(4-chlorobenzylthio)-4-phenyl-thieno[2,3-d]pyrimidine-6-carboxylate Cyclization of S-p-chlorobenzylisothiourea HCl (237 mg), benzaldehyde (203 μl) and ethyl cyanoacetate (117 μl), treatment of the product with POCl$_3$ and subsequent reaction with ethyl 2-mercaptoacetate were performed according to the methods described in example 1.

Yield: 34 mg. MS-ESI: [M+H]$^+$=456.2. TLC: $R_f$=0.74, silica gel, dichloromethane.

Example 11

Ethyl 5-Amino-2-ethoxycarbonylmethylthio-4-(3-methoxyphenyl)-thieno[2,3-d]pyrimidine-6-carboxylate Cyclization of S-methylisothiourea sulfate (139 mg), 3-methoxybenzaldehyde (243 μl) and ethyl cyanoacetate (112 μl), treatment of the product with POCl$_3$ and subsequent reaction with ethyl 2-mercaptoacetate were performed according to the methods described in example 1.

Yield: 37 mg. MS-ESI: [M+H]$^+$=448.2. TLC: $R_f$=0.12, silica gel, dichloromethane.

Example 12

Ethyl 5-Amino-2-methylthio-4-(3-thienyl)-thieno[2,3-d]pyrimidine-6-carboxylate

Cyclization of S-methylisothiourea sulfate (695 mg), thiophene-3-carboxaldehyde (910 μl) and ethyl cyanoacetate (580 µl), treatment of the product with POCl$_3$ and subsequent reaction with ethyl 2-mercaptoacetate were performed according to the methods described in example 1.

Yield: 176 mg. MS-ESI: [M+H]$^+$=352.2. TLC: R$_f$=0.52, silica gel, dichloromethane.

Example 13

Ethyl 5-Amino-4-(3-furyl)-2-methylthio-thieno[2,3-d]pyrimidine-6-carboxylate

Cyclization of S-methylisothiourea sulfate (139 mg), 3-furaldehyde (129 µl) and ethyl cyanoacetate (112 µl), treatment of the product with POCl$_3$ and subsequent reaction with ethyl 2-mercaptoacetate were performed according to the methods described in example 1.

Yield: 32 mg. MS-ESI: [M+H]$^+$=336.2. TLC: R$_f$=0.38, silica gel, dichloromethane.

Example 14

Ethyl 5-Amino-4-(2-fluorophenyl)-2-methylthio-thieno[2,3-d]pyrimidine-6-carboxylate Cyclization of S-methylisothiourea sulfate (139 mg), 2-fluorobenzaldehyde (211 µl) and ethyl cyanoacetate (112 µl), treatment of the product with POCl$_3$ and subsequent reaction with ethyl 2-mercaptoacetate were performed according to the methods described in example 1.

Yield: 91 mg. MS-ESI: [M+H]$^+$=364.0. TLC: R$_f$=0.51, silica gel, dichloromethane.

Example 15

Ethyl 5-Amino-4-(3-bromophenyl)-2-methylthio-thieno[2,3-d]pyrimidine-6-carboxylate Cyclization of S-methylisothiourea sulfate (139 mg), 3-bromobenzaldehyde (233 µl) and ethyl cyanoacetate (112 µl), treatment of the product with POCl$_3$ and subsequent reaction with ethyl 2-mercaptoacetate were performed according to the methods described in example 1.

Yield: 170 mg. MS-ESI: [M+H]$^+$=426.2. TLC: R$_f$=0.70, silica gel, dichloromethane.

Example 16

Ethyl 5-Amino-2-methylthio-4-(4-pyridyl)-thieno[2,3-d]pyrimidine-6-carboxylate

Cyclization of S-methylisothiourea sulfate (139 mg), 4-pyridinecarboxaldehyde (191 µl) and ethyl cyanoacetate (112 µl), treatment of the product with POCl$_3$ and subsequent reaction with ethyl 2-mercaptoacetate were performed according to the methods described in example 1.

Yield: 29 mg. MS-ESI: [M+H]$^+$=347.2. TLC: R$_f$=0.54, silica gel, dichloromethane.

Example 17

Ethyl 5-Amino-2-methylthio-4-(2-pyridyl)-thieno[2,3-d]pyrimidine-6-carboxylate

Cyclization of S-methylisothiourea sulfate (139 mg), 2-pyridinecarboxaldehyde (190 µl) and ethyl cyanoacetate (112 µl), treatment of the product with POCl$_3$ and subsequent reaction with ethyl 2-mercaptoacetate were performed according to the methods described in example 1.

Yield: 73 mg. MS-ESI: [M+H]$^+$=347.2. TLC: R$_f$=0.50, silica gel, dichloromethane.

Example 18

Ethyl 5-Amino-2-methylthio-4-(2-thienyl)-thieno[2,3-d]pyrimidine-6-carboxylate

Cyclization of S-methylisothiourea sulfate (139 mg), thiophene-2-carboxaldehyde (189 µl) and ethyl cyanoacetate (112 µl), treatment of the product with POCl$_3$ and subsequent reaction with ethyl 2-mercaptoacetate were performed according to the methods described in example 1.

Yield: 106 mg. MS-ESI: [M+H]$^+$=381.2. TLC: R$_f$=0.67, silica gel, dichloromethane.

Example 19

Ethyl 5-Amino-2,4-diphenyl-thieno[2,3-d]pyrimidine-6-carboxylate

Cyclization of benzamidine.HCl (156 mg), benzaldehyde (203 µl) and ethyl cyanoacetate (117 µl), treatment of the product with POCl$_3$ and subsequent reaction with ethyl 2-mercaptoacetate were performed according to the methods described in example 1.

Yield: 101 mg. MS-ESI: [M+H]$^+$=376.2. TLC: R$_f$=0.60, silica gel, dichloromethane.

Example 20

Ethyl 5-Amino-2-phenyl-(3-thienyl)-thieno[2,3-d]pyrimidine-6-carboxylate

Cyclization of benzamidine.HCl (156 mg), thiophene-3-carboxaldehyde (183 µl) and ethyl cyanoacetate (117 µl), treatment of the product with POCl$_3$ and subsequent reaction with ethyl 2-mercaptoacetate were performed according to the methods described in example 1.

Yield: 203 mg. MS-ESI: [M+H]$^+$=382.0. TLC: R$_f$=0.65, silica gel, dichloromethane.

Example 21

Ethyl 5-Amino-4-(3-furyl)-2-phenyl-thieno[2,3-d]pyrimidine-6-carboxylate

Cyclization of benzamidine.HCl (156 mg), 3-furaldehyde (129 µl) and ethyl cyanoacetate (117 µl), treatment of the product with POCl$_3$ and subsequent reaction with ethyl 2-mercaptoacetate were performed according to the methods described in example 1.

Yield: 157 mg. MS-ESI: [M+H]$^+$=366.2. TLC: R$_f$=0.55, silica gel, dichloromethane.

Example 22

Ethyl 5-Amino-4-(3-methoxphenyl)-2-phenyl-thieno[2,3-d]pyrimidine-6-carboxylate

Cyclization of benzamidine.HCl (157 mg), 3-methoxybenzaldehyde (243 µl) and ethyl cyanoacetate (112 µl), treatment of the product with POCl$_3$ and subsequent reaction with ethyl 2-mercaptoacetate were performed according to the methods described in example 1.

Yield: 164 mg. MS-ESI: [M+H]$^+$=406.2. TLC: R$_f$=0.66, silica gel, dichloromethane.

Example 23

Ethyl 5-Amino-2-(4-chlorophenyl)-4-phenyl-thieno[2,3-d]pyrimidine-6-carboxylate

Cyclization of 4-chlorobenzamidine (772 mg), benzaldehyde (1.0 ml) and ethyl cyanoacetate (1.07 ml), treatment of the product with POCl₃ and subsequent reaction with ethyl 2-mercaptoacetate were performed according to the methods described in example 1.

Yield: 300 mg. MS-ESI: [M+H]⁺=410.0. TLC: R_f=0.77, silica gel, dichloromethane/heptane=3/1 v/v.

Example 24

Ethyl 5-Amino-4-phenyl-2-(2-thienyl)-thieno[2,3-d]pyrimidine-6-carboxylate

Cyclization of 2-amidinothiophene.HCl (162 mg), benzaldehyde (203 µl) and ethyl cyanoacetate (117 µl), treatment of the product with POCl₃ and subsequent reaction with ethyl 2-mercaptoacetate were performed according to the methods described in example 1.

Yield: 159 mg. MS-ESI: [M+H]⁺=382.0. TLC: R_f=0.80, silica gel, dichloromethane.

Example 25

Ethyl 5-Amino-2-(2-thienyl)-4-(3-thienyl)-thieno[2,3-d]pyrimidine-6-carboxylate

Cyclization of 2-amidinothiophene.HCl (162 mg), thiophene-2-carboxaldehyde (183 µl) and ethyl cyanoacetate (117 µl), treatment of the product with POCl₃ and subsequent reaction with ethyl 2-mercaptoacetate were performed according to the methods described in example 1.

Yield: 139 mg. MS-ESI: [M+H]⁺=388.2. TLC: R_f=0.60, silica gel, dichloromethane.

Example 26

Ethyl 5-Amino-4-(3-furyl)-2-(2-thienyl)-thieno[2,3-d]pyrimidine-6-carboxylate

Cyclization of 2-amidinothiophene.HCl (162 mg), 3-furaldehyde (129 µl) and ethyl cyanoacetate (117 µl), treatment of the product with POCl₃ and subsequent reaction with ethyl 2-mercaptoacetate were performed according to the methods described in example 1.

Yield: 131 mg. MS-ESI: [M+H]⁺=372.0. TLC: R_f=0.90, silica gel, dichloromethane.

Example 27

Ethyl 5-Amino-4-(3-methoxyphenyl)-2-(2-thienyl)-thieno[2,3-d]pyrimidine-6-carboxylate Cyclization of 2-amidinothiophene.HCl (162 mg), 3-methoxybenzaldehyde (243 µl) and ethyl cyanoacetate (112 µl), treatment of the product with POCl₃ and subsequent reaction with ethyl 2-mercaptoacetate were performed according to the methods described in example 1.

Yield: 186 mg. MS-ESI: [M+H]⁺=412.2. TLC: R_f=0.61, silica gel, dichloromethane.

Example 28

Ethyl 5-Amino-4-phenyl-2-(4-pyridyl)-thieno[2,3-d]pyrimidine-6-carboxylate

Cyclization of 4-amidinopyridine.HCl (157 mg), benzaldehyde (203 µl) and ethyl cyanoacetate (117 µl), treatment of the product with POCl₃ and subsequent reaction with ethyl 2-mercaptoacetate were performed according to the methods described in example 1.

Yield: 121 mg. MS-ESI: [M+H]⁺=377.2. TLC: R_f=0, silica gel, dichloromethane.

Example 29

Ethyl 5-Amino-2-(4-pyridyl)-4-(3-thienyl)-thieno[2,3-d]pyrimidine-6-carboxylate

Cyclization of 4-amidinopyridine.HCl (157 mg), thiophene-3-carboxaldehyde (183 µl) and ethyl cyanoacetate (117 µl), treatment of the product with POCl₃ and subsequent reaction with ethyl 2-mercaptoacetate were performed according to the methods described in example 1.

Yield: 12 mg. MS-ESI: [M+H]⁺=283.0. TLC: R_f=0.85, silica gel, dichloromethane.

Example 30

Ethyl 5-Amino-4-(3-furyl)-2-(4-pyridyl)-thieno[2,3-d]pyrimidine-6-carboxylate

Cyclization of 4-amidinopyridine.HCl (157 mg), 3-furaldehyde (129 µl) and ethyl cyanoacetate (117 µl), treatment of the product with POCl₃ and subsequent reaction with ethyl 2-mercaptoacetate were performed according to the methods described in example 1.

Yield: 51 mg. MS-ESI: [M+H]⁺=367.0. TLC: R_f=0.05, silica gel, dichloromethane.

Example 31

Ethyl 5-Amino-4-(3-methoxyphenyl)-2-(4-pyridyl)-thieno[2,3-d]pyrimidine-6-carboxylate Cyclization of 4-amidinopyridine.HCl (157 mg), 3-methoxybenzaldehyde (243 µl) and ethyl cyanoacetate (112 µl), treatment of the product with POCl₃ and subsequent reaction with ethyl 2-mercaptoacetate were performed according to the methods described in example 1.

Yield: 153 mg. MS-ESI: [M+H]⁺=407.2. TLC: R_f=0.42, silica gel, dichloromethane/jmethanol 95/5 v/v.

Example 32

Ethyl 5-Amino-2-methylamino-4-phenyl-thieno[2,3-d]pyrimidine-6-carboxylate

Cyclization of 1-methylguanidine.HCl (110 mg), benzaldehyde (203 µl) and ethyl cyanoacetate (117 µl), treatment of the product with POCl₃ and subsequent reaction with ethyl 2-mercaptoacetate were performed according to the methods described in example 1.

Yield: 48 mg. MS-ESI: [M+H]⁺=329.2. TLC: R_f=0.85, silica gel, dichloromethane/methanol 95/5 v/v.

Example 33

Ethyl 5-Amino-2-methylthio-4-phenyl-thieno[2,3-d]pyrimidine-6-carboxylate

Cyclization of S-methylisothiourea sulfate (8.35 g), benzaldehyde (12.2 ml) and ethyl cyanoacetate (6.70 ml), treatment of the product with POCl₃ and subsequent reaction with ethyl 2-mercaptoacetate were performed according to the methods described in example 1.

Yield: 7.98 g. MS-ESI: [M+H]⁺=346.2. TLC: R_f=0.92, silica gel, dichloromethane.

Example 34

5-Amino-2-methylthio-4-phenyl-thieno[2,3-d]pyrimidine-6-carboxylic Acid

Lithium hydroxide (923 mg) was added to a stirred solution of 760 mg ethyl 5-amino-2-methylthio-4-phenylthieno[2,3-d]pyrimidine-6-carboxylate (see example 33) in dioxane/water=9/1 (v/v) and the mixture was heated at 80° C. for 24 h. The reaction mixture was poured into water and extracted with ethyl acetate at pH 2. The organic layer was washed with water and brine and dried over sodium sulfate. The filtrate was evaporated to dryness.

Yield: 766 mg. MS-ESI: [M+H]$^+$=318.0. TLC: $R_f$=0.49, silica gel, dichloromethane/methanol=9/1 v/v.

Example 35

Phenyl 5-Amino-2-methylthio-4-phenyl-thieno[2,3-d]pyrimidine-6-carboxylate

To a stirred solution of 40 mg 5-amino-2-methylthio-4-phenyl-thieno[2,3-d]pyrimidine-6-carboxylic acid, which was synthesized via the method described in example 34, in dichloromethane (2 ml) was added N,N-diisopropylethylamine (100 µl), phenol (13 mg) and bromotripyrrolidinophosphonium hexafluorophosphate (79 mg). After 20 h water (2 ml) was added and the mixture was vigorously stirred and subsequently filtered over a PE-filter. The organic phase was concentrated in vacuo and the residue was chromatographed on silicagel (Isolute, 2 g) in dichloromethane as eluent.

Yield: 16 mg. MS-ESI: [M+H]$^+$=394.2. TLC: $R_f$=0.32, silica gel, dichloromethane.

Example 36 n-Butyl 5-Amino-2-methylthio-4-phenyl-thieno[2,3-d]pyrimidine-6-carboxylate

Esterification of 5-amino-2-methylthio-4-phenyl-thieno[2,3-d]pyrimidine-6-carboxylic acid (40 mg) with n-butanol (13 µl) was accomplished according to the procedure described in example 35. The residue was chromatographed on silicagel (Isolute, 2 g) in dichloromethane as eluent.

Yield: 7 mg. MS-ESI: [M+H]$^+$=374.2. TLC: $R_f$=0.66, silica gel, dichloromethane.

Example 37

Cyclohexyl 5-Amino-2-methylthio-4-phenyl-thieno[2,3-d]pyrimidine-6-carboxylate

Esterification of 5-amino-2-methylthio-4-phenyl-thieno[2,3-d]pyrimidine-6-carboxylic acid (40 mg) with cyclohexanol (14 µl) was accomplished according to the procedure described in example 35. The residue was chromatographed on silicagel (Isolute, 2 g) in dichloromethane as eluent.

Yield: 14 mg. MS-ESI: [M+H]$^+$=400.2. TLC: $R_f$=0.66, silica gel, dichloromethane.

Example 38

Benzyl 5-Amino-2-methylthio-4-phenyl-thieno[2,3-d]pyrimidine-6-carboxylate

Esterification of 5-amino-2-methylthio-4-phenyl-thieno[2,3-d]pyrimidine-6-carboxylic acid (40 mg) with benzylalcohol (14 µl) was accomplished according to the procedure described in example 35. The residue was chromatographed on silicagel (Isolute, 2 g) in dichloromethane as eluent.

Yield: 10 mg. MS-ESI: [M+H]$^+$=408.2. TLC: $R_f$=0.66, silica gel, dichloromethane.

Example 39

3-Bromo-2-R-methyl-1-propyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 3-bromo-2-R-methylpropan-1-ol (14 µl) was accomplished according to the procedure described in example 35. The residue was chromatographed on silicagel (Isolute, 2 g) in dichloromethane as eluent.

Yield: 5 mg. MS-ESI: [M+H]$^+$=454.2. TLC: $R_f$=0.66, silica gel, dichloromethane.

Example 40

4-Methoxphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 4-methoxyphenol (17 mg) was accomplished according to the procedure described in example 35. The residue was chromatographed on silicagel (Isolute, 2 g) in heptane/dichloromethane 1/1 (v/v) as eluent.

Yield: 26 mg. MS-ESI: [M+H]$^+$=424.2. TLC: $R_f$=0.64, silica gel, dichloromethane.

Example 41

3-Methoxyphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 3-methoxyphenol (17 mg) was accomplished according to the procedure described in example 35. The residue was chromatographed on silicagel (Isolute, 2 g) in heptane/dichloromethane 1/1 (v/v) as eluent.

Yield: 29 mg. MS-ESI: [M+H]$^+$=424.2. TLC: $R_f$=0.60, silica gel, dichloromethane.

Example 42

2-Methoxyphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 2-methoxyphenol (17 mg) was accomplished according to the procedure described in example 35. The residue was chromatographed on silicagel (Isolute, 2 g) in heptane/dichloromethane 1/1 (v/v) as eluent.

Yield: 19 mg. MS-ESI: [M+H]$^+$=424.2. TLC: $R_f$=0.60, silica gel, dichloromethane.

Example 43

2,3-Dimethoxyphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 2,3-dimethoxyphenol (21 mg) was accomplished according to the procedure described in example 35. The residue was chromatographed on silicagel (Isolute, 2 g) in heptane/dichloromethane 1/1 (v/v) as eluent.

Yield: 12 mg. MS-ESI: [M+H]$^+$=454.2. TLC: $R_f$=0.36, silica gel, dichloromethane.

Example 44

2,4-Dimethoxyphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 2,4- dimethoxyphenol (21 mg) was accomplished according to the procedure described in example 35. The residue was chromatographed on silicagel (Isolute, 2 g) in heptane/dichloromethane 1/1 (v/v) as eluent.

Yield: 20 mg. MS-ESI: [M+H]$^+$=454.4. TLC: R=0.38, silica gel, dichloromethane.

Example 45

3,5-Dimethoxyphenyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 3,5-dimethoxyphenol (21 mg) was accomplished according to the procedure described in example 35. The residue was chromatographed on silicagel (Isolute, 2 g) in heptane/dichloromethane 1/1 (v/v) as eluent.

Yield: 18 mg. MS-ESI: [M+H]$^+$=454.2. TLC: $R_f$=0.60, silica gel, dichloromethane.

Example 46

Isopropyl 5-Amino-2-methylthio-4-phenyl-thieno[2,3-d]pyrimidine-6-carboxylate

Esterification of 5-amino-2-methylthio-4-phenyl-thieno[2,3-d]pyrimidine-6-carboxylic acid (40 mg) with 2-propanol (10 µl) was accomplished according to the procedure described in example 35. The residue was chromatographed on silicagel (Isolute, 2 g) in heptane/dichloromethane 1/1 (v/v) as eluent.

Yield: 12 mg. MS-ESI: [M+H]$^+$=360.2. TLC: $R_f$=0.66, silica gel, dichloromethane.

Example 47

2-Thienylmethyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 2-thiophenemethanol (17 µl) was accomplished according to the procedure described in example 35. The residue was chromatographed on silicagel (Isolute, 2 g) in heptane/dichloromethane 1/1 (v/v) as eluent.

Yield: 18 mg. MS-ESI: [M+H]$^+$=414.2. TLC: $R_f$=0.74, silica gel, dichloromethane.

Example 48

3-Thienylmethyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 3-thiophenemethanol (15 mg) was accomplished according to the procedure described in example 35. The residue was chromatographed on silicagel (Isolute, 2 g) in heptane/dichloromethane 1/1 (v/v) as eluent.

Yield: 12 mg. MS-ESI: [M+H]$^+$=414.2. TLC: $R_f$=0.74, silica gel, dichloromethane.

Example 49

2-Adamantylmethyl 5-Amino-2-methylthio-4-phenyl-thieno[2,3-d]pyrimidine-6-carboxylate Esterification of 5-amino-2-methylthio-4-phenyl-thieno[2,3-d]pyrimidine-6-carboxylic acid (40 mg) with 1-adamantanemethanol (22 mg) was accomplished according to the procedure described in example 35. The residue was chromatographed on silicagel (Isolute, 2 g) in heptane/dichloromethane 1/1 (v/v) as eluent.

Yield: 15 mg. MS-ESI: [M+H]$^+$=466.2. TLC: $R_f$=0.81, silica gel, dichloromethane.

Example 50

2-N-Pyrrolidino-1-ethyl 5-Amino-2-methylthio-4-phenyl-thieno[2,3-d]pyrimidine-6-carboxylate To a stirred solution of 40 mg 5-amino-2-methylthio-4-phenyl-thieno[2,3-d]pyrimidine-6-carboxylic acid, which was synthesized via the method described in example 34, in dichloromethane (2 ml) was added N,N-diisopropylethylamine (40 µl), 1-(2-hydroxyethyl)pyrrolidine (20 µl) and O-(benzotriazol-1-yl)-N,N,N',N'-tetramethyluronium tetrafluoroborate (40 mg). After 20 h the solvent was evaporated and the residue was chromatographed on silicagel (Isolute, 2 g) in heptane/dichloromethane=100/0 (v/v)→0/100 (v/v) as eluent.

Yield: 13 mg. MS-ESI: [M+H]$^+$=415.0. TLC: $R_f$=0.07, silica gel, dichloromethane/methanol=98/2 v/v.

Example 51

Isopropyl 5-Amino-4-(3-methoxyphenyl)-2-phenyl-thieno[2,3-d]pyrimidine-6-carboxylate Ethyl 5-amino-4-(3-methoxyphenyl)-2-phenyl-thieno[2,3-d]pyrimidine-6-carboxylate (see example 22) was first hydrolyzed to the corresponding acid (52 mg) using the method described in example 34 and subsequently esterified with 2-propanol (12 µl) to the corresponding ester according to example 35. The residue was chromatographed on silicagel (Isolute, 2 g) in heptane/dichloromethane 1/1 (v/v) as eluent.

Yield: 18 mg. MS-ESI: [M+H]$^+$=420.2. TLC: $R_f$=0.66, silica gel, dichloromethane.

Example 52

Phenyl 5-Amino-4-(3-methoxyphenyl)-2-phenyl-thieno[2,3-d]pyrimidine-6-carboxylate Esterification of 5-amino-4-(3-methoxyphenyl)-2-phenyl-thieno[2,3-d]pyrimidine-6-carboxylic acid (52 mg) with phenol (15 mg) was accomplished according to the procedures described in example 51. The residue was chromatographed on silicagel (Isolute, 2 g) in heptane/dichloromethane 1/1 (v/v) as eluent.

Yield: 36 mg. MS-ESI: [M+H]$^+$=454.4. TLC: $R_f$=0.73, silica gel, dichloromethane.

Example 53

Isopropyl 5-Amino-2-(2-thienyl)-3-thienyl)-thieno[2,3-d]pyrimidine-6-carboxylate Ethyl 5-amino-2-(2-thienyl)-(3-thienyl)-thieno[2,3-d]pyrimidine-6-carboxylate (see example 25) was first hydrolyzed to the corresponding acid (45 mg) using the methods described in example 34 and subsequently esterified with 2-propanol (11 µl) to the corresponding ester according to example 35. The residue was chromatographed on silicagel (Isolute, 2 g) in heptane/dichloromethane 1/1 (v/v) as eluent.

Yield: 11 mg. MS-ESI: [M+H]$^+$=402.2. TLC: $R_f$=0.66, silica gel, dichloromethane.

Example 54

Phenyl 5-Amino-2-(2-thienyl)-4-(3-thienyl)-thieno[2,3-d]pyrimidine-6-carboxylate Esterification of 5-amino-2-(2-thienyl)-4-(3-thienyl)-thieno[2,3-d]pyrimidine-6-carboxylic acid (45 mg) with phenol (13 mg) was accomplished according to the procedures described in example 53. The residue was chromatographed on silicagel (Isolute, 2 g) in heptane/dichloromethane 1/1 (v/v) as eluent.

Yield: 13 mg. MS-ESI: [M+H]$^+$=436.4. TLC: R$_f$=0.73, silica gel, dichloromethane.

Example 55

Isopropyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with 2-aminopropane (12 μl) was accomplished according to the procedure described in example 35. The residue was chromatographed on silicagel (Isolute, 2 g) in dichloromethane as eluent.

Yield: 7 mg. MS-ESI: [M+H]$^+$=359.2. TLC: R$_f$=0.23, silica gel, dichloromethane.

Example 56

Benzyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with benzylamine (15 μl) was accomplished according to the procedure described in example 35. The residue was chromatographed on silicagel (Isolute, 2 g) in dichloromethane as eluent.

Yield: 32 mg. MS-ESI: [M+H]$^+$=407.2. TLC: R$_f$=0.24, silica gel, dichloromethane.

Example 57 n-Butyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with 1-aminobutane (13 μl) was accomplished according to the procedure described in example 35. The residue was chromatographed on silicagel (Isolute, 2 g) in dichloromethane as eluent.

Yield: 18 mg. MS-ESI: [M+H]$^+$=373.2. TLC: R$_f$=0.25, silica gel, dichloromethane.

Example 58

Cyclopropyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with cyclopropylamine (9 μl) was accomplished according to the procedure described in example 35. The residue was chromatographed on silicagel (Isolute, 2 g) in dichloromethane as eluent.

Yield: 9 mg. MS-ESI: [M+H]$^+$=357.2. TLC: R$_f$=0.14, silica gel, dichloromethane.

Example 59

Cyclohexyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with cyclohexylamine (16 μl) was accomplished according to the procedure described in example 35. The residue was chromatographed on silicagel (Isolute, 2 g) in dichloromethane as eluent.

Yield: 11 mg. MS-ESI: [M+H]$^+$=399.2. TLC: R$_f$=0.32, silica gel, dichloromethane.

Example 60

4-Methoxybenzyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 4-methoxybenzylamine (18 μl) was accomplished according to the procedure described in example 35. The residue was chromatographed on silicagel (Isolute, 2 g) in dichloromethane as eluent.

Yield: 25 mg. MS-ESI: [M+H]$^+$=437.2. TLC: R$_f$=0.20, silica gel, dichloromethane.

Example 61

1-Naphthylmethyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 1-naphthylmethylamine (20 μl) was accomplished according to the procedure described in example 35. The residue was chromatographed on silicagel (Isolute, 2 g) in dichloromethane as eluent.

Yield: 20 mg. MS-ESI: [M+H]$^+$=457.2. TLC: R$_f$=0.32, silica gel, dichloromethane.

Example 62

Phenyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (39 mg) with aniline (909 μl) was accomplished according to the procedure described in example 35. The residue was chromatographed on silicagel (Isolute, 2 g) in dichloromethane as eluent.

Yield: 37 mg. MS-ESI: [M+H]$^+$=393.0. TLC: R=0.95, silica gel, ethyl acetate/pyridine/acetic acid/water=363/20/6/11 v/v/v/v.

Example 63

2-Thienylmethyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 2-thiophenemethylamine (14 μl) was accomplished according to the procedure described in example 35 and the crude product was purified by chromatography on silicagel (Isolute, 2 g) in heptane/dichloromethane=1/1 (v/v) as eluent.

Yield: 12 mg. MS-ESI: [M+H]$^+$=413.2. TLC: R$_f$=0.23, silica gel, dichloromethane.

Example 64

1-Adamantylmethyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 1-adamantanemethylamine (22 μl) was accomplished according to the procedure described in example 35 and the crude product was purified by chromatography on silicagel (Isolute, 2 g) in heptane/dichloromethane=1/1 (v/v) as eluent.

Example 65 n-Heptyl 5-Amino-2-methylthio-4-phenyl-thieno[2,3-d]pyrimidine-6-carboxamide

Reaction of 5-amino-2-methylthio-4-phenyl-thieno[2,3-d]pyrimidine-6-carboxylic acid (40 mg) with 1-aminoheptane (25 µl) was accomplished according to the procedure described in example 50. The residue was chromatographed on silicagel (Isolute, 2 g) in heptane/dichloromethane 1/1 (v/v) as eluent.

Yield: 37 mg. MS-ESI: $[M+H]^+$=415.2. TLC: $R_f$=0.87, silica gel, dichloromethane/methanol=98/2 v/v.

Example 66

3-Phenyl-1-propyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 3-phenyl-1-propylamine (24 µl) was accomplished according to the procedure described in example 50. The residue was chromatographed on silicagel (Isolute, 2 g) in heptane/dichloromethane 1/1 (v/v) as eluent.

Yield: 32 mg. MS-ESI: $[M+H]^+$=435.2. TLC: $R_f$=0.83, silica gel, dichloromethane/methanol=98/2 v/v.

Example 67

1,1-Diethoxy-4-butyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with 4,4-diethoxybutylamine (30 µl) was accomplished according to the procedure described in example 50. The residue was chromatographed on silicagel (Isolute, 2 g) in heptane/dichloromethane 1/1 (v/v) as eluent.

Yield: 47 mg. MS-ESI: $[M+H]^+$=461.2. TLC: $R_f$=0.38, silica gel, dichloromethane/methanol=98/2 v/v.

Example 68

(3R)-(−)-1-Benzyl-3-pyrrolidinylamino 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with (3R)-(−)-1-benzyl-3-aminopyrrolidine (29 µl) was accomplished according to the procedure described in example 50. The residue was chromatographed on silicagel (Isolute, 2 g) in heptane/dichloromethane 1/1 (v/v) as eluent.

Yield: 50 mg. MS-ESI: $[M+H]^+$=476.2. TLC: $R_f$=0.21, silica gel, dichloromethane/methanol=98/2 v/v.

Example 69

3-Methoxycarbonyl-1-propyl 5-Amino-2-methylthio-4-phenyl-thieno[2,3-d]pyrimidine-6-carboxamide Reaction of 5-amino-2-methylthio-4-phenyl-thieno[2,3-d]pyrimidine-6-carboxylic acid (40 mg) with methyl 4aminobutyrate (26 mg) was accomplished according to the procedure described in example 50. The residue was chromatographed on silicagel (Isolute, 2 g) in heptane/dichloromethane 1/1 (v/v) as eluent.

Yield: 39 mg. MS-ESI: $[M+H]^+$=417.0. TLC: $R_f$=0.46, silica gel, dichloromethane/methanol=98/2 v/v.

Example 70

Isopropyl 5-Amino-4-(3-methoxyphenyl)-2-methylthio-thieno[2,3-d]pyrimidine-6-carboxamide Ethyl 5-amino-4-(3-methoxyphenyl)-2-methylthio-thieno[2,3-d]pyrimidine-6-carboxylate (see example 1) was first hydrolyzed to the corresponding acid (248 mg) using the method described in example 34 and subsequently reacted with 2-aminopropane (111 µl) to the corresponding amide according to example 50. The title compound was purified by chromatography on silicagel in dichloromethane/methanol=98/2 (v/v) as eluent followed by crystallisation from ethanol.

Yield: 147 mg. MS-ESI: $[M+H]^+$=389.0. TLC: $R_f$=0.19, silica gel, dichloromethane.

Example 71

Isopropyl 5-Amino-4-(3-methoxylphenyl)-2-phenyl-thieno[2,3-d]pyrimidine-6-carboxamide Ethyl 5-amino-4-(3-methoxyphenyl)-2-phenyl-thieno[2,3-d]pyrimidine-6-carboxylate (see example 22) was first hydrolyzed to the corresponding acid (52 mg) using the method described in example 34 and subsequently reacted with 2-aminopropane (13 µl) to the corresponding amide according to example 35. The residue was chromatographed on silicagel (Isolute, 2 g) in heptane/dichloromethane 1/1 (v/v) as eluent.

Yield: 12 mg. MS-ESI: $[M+H]^+$=419.4. TLC: $R_f$=0.17, silica gel, dichloromethane.

Example 72

Isopropyl 5-Amino-4-(3-methoxyphenyl)-2-(2-thienyl)-thieno[2,3-d]pyrimidine-6-carboxamide Ethyl 5-amino-4-(3-methoxyphenyl)-2-(2-thienyl)-thieno[2,3-d]pyrimidine-6-carboxylate (see example 27) was first hydrolyzed to the corresponding acid (464 mg) using the method described in example 34 and subsequently reacted with 2-aminopropane (190 µl) to the corresponding amide according to example 50. The title compound was chromatographed on silicagel in dichloromethane/methanol=98/2 (v/v) as eluent.

Yield: 332 mg. MS-ESI: $[M+H]^+$=425.2. TLC: $R_f$=0.23, silica gel, dichloromethane.

Example 73

Isopropyl 5-Amino-2-(2-thienyl)-4-(3-thienyl)-thieno[2,3-d]pyrimidine-6-carboxamide Ethyl 5-amino-2-(2-thienyl)-4-(3-thienyl)-thieno[2,3-d]pyrimidine-6-carboxylate (see example 25) was first hydrolyzed to the corresponding acid (753 mg) using the method described in example 34 and subsequently reacted with 2-aminopropane (326 µl) to the corresponding amide according to example 50. The title compound was chromatographed on silicagel in dichloromethane/methanol=98/2 (v/v).

Yield: 646 mg. MS-ESI: $[M+H]^+$=401.2. TLC: $R_f$=0.29, silica gel, dichloromethane.

Example 74

Ethyl 5-Amino-7-methyl-2-methylthio-4-phenyl-pyrrolo[2,3-d]pyrimidine-6-carboxylate (a). 5-Cyano-6-(ethoxycarbonylmethyl)(methyl)amino-2-methylthio-4-phenylpyrridine A mixture of sodium bicarbonate (160 mg) and ethyl N-methylglycinate.HCl (438 mg) in ethanol was heated under reflux. After 2 h 6-chloro-5-canyo-2-methylthio-4-phenylpyrimidine (100 mg, see example 1b) was added and the reaction mixture was refluxed for another 2.5 h. The solids were removed by filtration after which the product crystallized from the filtrate.

Yield: 65 mg. MS-ESI: $[M+H]^+=343.2$. TLC: $R_f=0.52$, silica gel, dichloromethane.

(b). Ethyl 5-Amino-7-methyl-2-methylthio-4-phenyl-pyrrolo[2,3-d]pyrimidine-6-carboxylate Sodium ethoxide (1.4N, 52 µl) was added to a stirred solution of 5-cyano-6-(ethoxycarbonylmethyl)(methyl)amino-2-methylthio-4-phenylpyrimidine in dry ethanol (1 ml). After 3 h at 60° C. the mixture was cooled to 0° C. in an ice bath and the solids were collected by filtration and dried in vacuo.

Yield: 40 mg MS-ESI: $[M+H]^+=343.2$. TLC: $R_f=0.53$, silica gel, dichloromethane.

Example 75

Ethyl 5-Amino-7-benzyl-2-methylthio-4-phenyl-pyrrolo[2,3-d]pyrimidine-6-carboxylate Condensation of 6-chloro-5-cyano-2-methylthio-4-phenylpyrimidine (100 mg) with ethyl N-benzylglycinate (0.45 ml) and subsequent cyclisation of purified 5-cyano-6-N-(ethyl N-benzylglycinate)-2-methylthio-4-phenylaminopyrimidine (chromatographed on silicagel in heptane/dichloromethane=1/3 (v/v)→1/0 (v/v)) to the end product was performed according to the procedures described in example 74.

Yield: 75 mg. MS-ESI: $[M+H]^+=419.2$. TLC: $R_f=0.78$, silica gel, dichloromethane.

Example 76

Ethyl 5-Amino-2-methylthio-4-(3-phenoxphenyl)-thieno[2,3-d]pyrimidine-6-carboxylate Cyclization of S-methylisothiourea sulfate (139 mg), 3-benoxybenzaldehyde (397 mg) and ethyl cyanoacetate (112 µl), treatment of the product with POCl$_3$ and subsequent reaction with ethyl 2-mercaptoacetate were performed according to the methods described in example 1. The title compound was purified by chromatography on silicagel in heptane/ethyl acetate=100/0 (v/v)→80/20 (v/v) as eluent.

Yield: 7.0 mg. MS-ESI: $[M+H]^+=438.0$. TLC: $R_f=0.61$, silica gel, dichloromethane.

Example 77

Ethyl 5-Amino-4-(3-n-butoxyphenyl)-2-methylthio-thieno[2,3-d]pyrimidine-6-carboxylate (a). 3-n-Butoxybenzaldehyde Diethyl azodicarboxylate (3.31 ml) was added dropwise to a cooled (0° C.) solution of 3-hydroxybenzaldehyde (2.44 g), n-butanol (1.83 ml) and triphenylphosphine (5.51 g) in tetrahydrofuran. After stirring at r.t. for 4 h, a solution of 2N sodium hydroxide (150 ml) was added and stirring was continued for 20 min. The reaction mixture was extracted with dichloromethane (150 ml). The organic layer was washed with water, 1% citric acid, water and brine, dried over sodium sulfate and concentrated in vacuo. To the crude product ethyl acetate (3×25 ml) was added and the solids were removed by filtration. The residue was chromatographed on silicagel in heptane/ethyl acetate=100/0 (v/v)→60/40 (v/v) as eluent.

Yield: 1.64 g. MS-ESI: $[M+H]^+=179.2$. TLC: $R_f=0.80$, silica gel, heptane/ethyl acetate=1/1 v/v.

(b). Ethyl 5-Amino-4-(3-n-butoxyphenyl)-2-methylthio-thieno[2,3-d]pyrimidine-6-carboxylate Cyclization of S-methylisothiourea sulfate (139 mg), 3-n-butoxybenzaldehyde (357 mg) and ethyl cyanoacetate (112 µl), treatment of the product with POCl$_3$ and subsequent reaction with ethyl 2-mercaptoacetate were performed according to the methods described in example 1. The title compound was purified by chromathography on silicagel in heptane/ethyl acetate=100/0 (v/v)→80/20 (v/v) as eluent and crystallisation from ethanol.

Yield: 78 mg. MS-ESI: $[M+H]^+=418.0$. TLC.: $R_f=0.61$, silica gel, dichloromethane.

Example 78

Ethyl 4-(3-[2-acetonethox]phenyl)-5-amino-2-methylthio-thieno[2,3-d]pyrimidine-6-carboxylate (a). 3-(2-Acetoxyethoxyl)benzaldehyde A catalytic amount of N,N-dimethylaminopyridine was added to a stirred solution of 3-(2-hydroxyethoxy) benzaldehyde (1.66 g) in acetic anhydride (9 ml) and pyridine (3 ml). After 2 h the reaction mixture was concentrated in vacuo, the residue was dissolved in ethyl acetate and washed with 0.5N hydrochloric acid, water, 5% sodium bicarbonate, water and brine, dried over sodium sulfate and evaporated to dryness.

Yield: 2.16 g. MS-ESI: $[M+H]^+=209.2$. TLC: $R_f=0.60$, silica gel, heptane/ethyl acetate=1/1 v/v.

(b). Ethyl 4-(3-[2-Acetoxyethoxy]phenyl)-5-amino-2-methylthio-thieno[2,3-d]pyrimidine-6-carboxylate Cyclization of S-methylisothiourea sulfate (139 mg), 3-(2-acetoxyethoxy)benzaldehyde (357 mg) and ethyl cyanoacetate (112 µl), treatment of the product with POCl$_3$ and subsequent reaction with ethyl 2-mercaptoacetate were performed according to the methods described in example 1. Reacetylation of the crude product (acetic anhydride/pyridine=3/1 (v/v), 4 h), concentration of the mixture and subsequent purification by chromatography on silicagel in dichloromethane yielded the title compound.

Yield: 6.0 mg. MS-ESI: $[M+H]^+=448.5$. TLC: $R_f=0.66$, silica gel, dichloromethane/methanol=98/2 v/v.

Example 79

Ethyl 5-Amino-2-methylthio-4-(3-n-octyloxyphenyl)-thieno[2,3-d]pyrimidine-6-carboxylate (a). 3-(n-Octyloxy)benzaldehyde 3-Hydroxybenzaldehyde (977 mg), 1-chlorooctane (1.35 ml) and cesium carbonate (3.9 g) were stirred in dioxane at 80° C. After 60 h the reaction mixture was cooled to r.t., the solids were removed by filtration and washed with dichloromethane. The combined filtrates were concentrated in vacuo, dissolved in ethyl acetate and washed with water and brine, dried over sodium sulfate, evaporated to dryness and purified by chromatography on silicagel in dichloromethane/methanol=100/0 (v/v)→98/2 (v/v).

Yield: 338 mg. MS-ESI: $[M+H]^+=235.2$. TLC: $R_f=0.95$, silica gel, dichloromethane/methanol=95/5 v/v.

(b). Ethyl 5-Amino-2-methylthio-4-(3-n-octyloxyphenyl)-thieno[2.3-d]pyrimidine-6-carboxylate Cyclization of S-methylisothiourea sulfate (139 mg), 3-n-octyloxybenzaldehyde (338 mg) and ethyl cyanoacetate (112 μl), treatment of the product with $POCl_3$ and subsequent reaction with ethyl 2-mercaptoacetate were performed according to the methods described in example 1. The pure title compound was obtained after chromatography on silicagel in dichloromethane/methanol=100/0 (v/v)→90/10 (v/v) as eluent.

Yield: 12 mg. MS-ESI: $[M+H]^+$=474.2. TLC: $R_f$=0.65, silica gel, dichloromethane.

Example 80

Ethyl 5-Amino-4-(3-[2-N-benzoylaminoethoxy]phenyl)-2-methylthio-thieno[2,3-d]pyrimidine-6-carboxylate Cyclization of S-methylisothiourea sulfate (278 mg), 3-(2-N-benzoylaminoethoxy)benzaldehyde (538 mg, synthesized from 3-hydroxybenzaldehyde (977 mg) and N-(2-chloroethyl)benzamide (1.47 g) via the procedure described in example 79a) and ethyl cyanoacetate (224 μl), treatment of the product with $POCl_3$ and subsequent reaction with ethyl 2-mercaptoacetate were performed according to the methods described in example 1. The pure title compound was obtained after chromatography on silicagel in dichloromethane/ethyl acetate=100/0 (v/v)→80/20 (v/v) as eluent.

Yield: 3.9 mg. MS-ESI: $[M+H]^+$=509.2. TLC: $R_f$=0.68, silica gel, dichloromethane/methanol=95/5 v/v.

Example 81

Ethyl 5-Amino-4-(3-{2-[5-methyl-2-phenylimidazol-4-yl]ethoxy}phenyl)-2-methylthio-thieno[2,3-d]pyrimidine-6-carboxylate (a). 4-Hydroxymethyl-5-methyl-2-phenylimidazole.HCl 2,3-Butanedione (30 ml) and a solution of sodium acetate (33 g) in water (80 ml) were added to a solution of benzamidine.HCl (66 g) in water (300 ml) at 0° C. After 1.5 h the solids were filtered off, washed with water and heated in 4N HCl (750 ml). The resulting clear solution was cooled in an ice-bath. The crystals were filtered off, washed with water and dried over potassium hydroxide at 50° C.

Yield: 44 g. Mp: 164–166° C.

(b). 4-Chloromethyl-5-methyl-2-phenylimidazole.HCl

A solution of thionylchloride (100 ml) in benzene (100 ml) was slowly added to a stirred suspension of 4-hydroxymethyl-5-methyl-2-phenylimidazole.HCl (44 g) in benzene (150 ml). After 2 h diethylether was added and the resulting solids were filtered off, washed with diethylether and dried in vacuo.

Yield: 60 g. Mp: 200–205° C.

(c). 4-Cyanomethyl-5-methyl-2-phenylimidazole

A solution of 4-chloromethyl-5-methyl-2-phenylimidazole.HCl (40.5 g) in dimethylsulfoxide (400 ml) was added to a stirred solution of sodium cyanide (80 g) in dimethylsulfoxide (600 ml) over a period of 30 min. After 20 h the solids were filtered off, washed with water and dried in vacuo.

Yield: 14 g. Mp: 97–100° C.

(d). 4-Ethoxycarbonylmethyl-5-methyl-2-phenylimidazole

Hydrochloric acid in ethanol (35%, 150 ml) was added to 4-cyanomethyl-5-methyl-2-phenylimidazole (20.5 g) and heated to reflux temperature. After 1 h the reaction mixture was poured into water (400 ml) and NaOH was added (pH>8), followed by extraction with dichloromethane (3 times). The combined organic layers were dried over sodium sulfate and evaporated to dryness in vacuo.

Yield: 17.3 g. Mp: 119–122° C.

(e). 4-Hydroxyethyl-5-methyl-2-phenylimidazole

A solution of 4-ethoxycarbonylmethyl-5-methyl-2-phenylimidazole (19.7 g) in tetrahydrofuran (100 ml) was added dropwise (in 45 min) to lithium aluminium hydride (10 g) in tetrahydrofuran (150 ml). After 2 h refluxing the reaction mixture was allowed to stand overnight at r.t. It was cooled in an ice bath and water (40 ml) and tetrahydrofuran (50 ml) were added. The solids were filtered off and washed with diethylether.

Yield: 20 g. Mp: 164–167° C.

(f). 4-Chloroethyl-5-methyl-2-phenylimidazole.HCl

A solution of thionylchloride (50 ml) in benzene (50 ml) was slowly added (1 h) to a stirred suspension of 4-hydroxyethyl-5-methyl-2-phenylimidazole (20 g) in benzene (250 ml) at 70° C. After 1.5 h the reaction mixture was concentrated in vacuo, dissolved in water (500 ml) and washed with diethylether. The pH was adjusted to >8 with ammonia and the mixture was extracted with diethylether (2 times). The combined organic layers were dried over sodium sulfate and evaporated in vacuo. The resulting oil was dissolved in ethanol. Hydrochloric acid in ethanol (35%, 2 ml) and diethylether were added, the solids were collected by filtration and recrystallized from ethanol.

Yield: 7.5 g. Mp: 188–190° C.

(g). Ethyl 5-Amino-4-(3-{2-[5-methyl-2-phenylimidazol-4-yl]ethoxy}phenyl)-2-methylthio-thieno[2,3-d]pyrimidine-6-carboxylate Cyclization of S-methylisothiourea sulfate (139 mg), 3-{2-[5-methyl-2-phenylimidazol-4-yl]ethoxy}benzaldehyde (496 mg, synthesized from 3-hydroxybenzaldehyde (489 mg) and 4-chloroethyl-5-methyl-2-phenylimidazole (1.03 g) via the procedure described in example 79a) and ethyl cyanoacetate (112 μl), treatment of the product with $POCl_3$ and subsequent reaction with ethyl 2-mercaptoacetate were performed according to the methods described in example 1. The pure title compound was obtained after chromathography on silicagel in dichloromethane/ethyl acetate=10010 (v/v)→70(30 (v/v) as eluent.

Yield: 9.2 mg. MS-ESI: $[M+H]^+$=546.2. TLC: $R_f$=0.43, silica gel, dichloromethane/methanol=95/5 v/v.

Example 82

Ethyl 5-Amino-2-methylthio-4-(3-[2-N-morpholinoethoxy]phenyl)-thieno[2,3d]pyrimidine-6-carboxylate Cyclization of S-methylisothiourea sulfate (209 mg), 3-(2-N-morpholinoethoxybenzaldehyde (705 mg, synthesized from 3-hydroxybenzaldehyde (1.17 g) and N-(2-chloroethyl)morpholine (1.44 g) via the procedure described in example 79a) and ethyl cyanoacetate (168 μl), treatment of the product with $POCl_3$ and subsequent reaction with ethyl 2-mercaptoacetate were performed according to the methods described in example 1.

Yield: 35.2 mg. MS-ESI: $[M+H]^+$=475.2. TLC: $R_f$=0.55, silica gel, dichloromethane/methanol=95/5 v/v.

Example 83

Ethyl 5-Amino-4-(3-[2-chloroethoxy]phenyl)-2-methylthio-thieno[2,3-d]pyrimidine-6-carboxylate Cyclization of S-methylisothiourea sulfate (209 mg), 3-(2-hydroxyethoxy)benzaldehyde (499 mg) and ethyl cyanoacetate (168 μl), treatment of the product with POCl$_3$ and subsequent reaction with ethyl 2-mercaptoacetate were performed according to the methods described in example 1. The pure title compound was obtained after chromatography on silicagel in dichloromethane as eluent.

Yield: 1.7 mg. MS-ESI: [M+H]$^+$=424.0. TLC: R$_f$=0.45, silica gel, dichloromethane.

Example 84

Ethyl 5-Amino-2-methylthio-4-(3-[2-{ethyloxycarbonylmethylthiol}ethoxy]phenyl)-thieno[2,3-d]pyrimidine-6-carboxylate Cyclization of S-methylisothiourea sulfate (209 mg), 3-(2-hydroxyethoxy)benzaldehyde (499 mg) and ethyl cyanoacetate (168 μl), treatment of the product with POCl$_3$ and subsequent reaction with ethyl 2-mercaptoacetate were performed according to the methods described in example 1. The pure title compound was obtained after chromatography on silicagel in dichloromethane as eluent.

Yield: 2.8 mg. MS-ESI: [M+H]$^+$=508.2. TLC: R$_f$=0.14, silica gel, dichloromethane.

Example 85

Ethyl 5-Hydroxy-2-methylthio-4-phenyl-thieno[2,3-d]pyrimidine-6-carboxylate (a). 5-Ethyoxycarbonyl-2-methylthio-4-phenyl-4,5-dihydro-6-oxopyrimidine A mixture of S-methylisothiourea sulfate (418 mg), benzaldehyde (320 μl), diethyl malonate (478 μl) and potassium carbonate (435 mg) in abs. ethanol (5 ml) was stirred at 50° C. for 4 h. The reaction mixture was evaporated to dryness, the residue was dissolved in ethyl acetate and washed with 0.5N hydrochloric acid, water, 5% sodium bicarbonate, water and brine, dried over sodium sulfate and evaporated to dryness.

Yield: 546 mg. MS-ESI: [M+H]$^+$=293.2. TLC: R$_f$=0.63, silica gel, dichloromethane/methanol 95/5 v/v.

(b). 5-Ethyloxycarbonyl-2-methylthio-4-phenyl-6-oxopyrimidine

A mixture of 5-ethyloxycarbonyl-2-methylthio-4-phenyl-4,5-dihydro-6-oxopyrimidine (273 mg) and 2,3-dichloro-5,6-dicyano-1,4-benzoquinone (200 mg) in isopropanol (5 ml) was stirred for 16 h. The reaction mixture was evaporated to dryness, the residue was dissolved in dichloromethane and stirred with 5% sodium thiosulfate for 5 min. The organic layer was washed with 5% sodium bicarbonate and water (2×), dried over sodium sulfate and evaporated to dryness. The pure title compound was obtained after chromatography on silicagel in dichloromethane/methanol 98/2 (v/v) as eluent.

Yield: 63 mg. MS-ESI: [M+H]$^+$=291.2. TLC: R$_f$=0.50, silica gel, dichloromethane/methanol 95/5 v/v.

(c). Ethyl 5-Hydroxy-2-methylthio-4-phenyl-thieno[2,3-d]pyrimidine-6-carboxylate Treatment of 5-ethyloxycarbonyl-2-methylthio-4-phenyl-6-oxopyrimidine (63 mg) with POCl$_3$ (304 μl) and subsequent reaction of the product with ethyl 2-mercaptoacetate were performed according to the methods described in example 1. The pure title compound was obtained after chromatography on silicagel in heptane\ethyl acetate 100/0→60/40 (v/v) as eluent.

Yield: 48 mg. MS-ESI: [M+H]$^+$=347.2. TLC: R$_f$=0.72, silica gel, dichloromethane.

Example 86

Ethyl 3-Amino-4,6-diphenyl-thieno[2,3-b]pyridine-2-carboxylate

Aldol condensation of acetophenone (2.33 ml) and benzaldehyde (2.24 ml), cyclisation of the α,β-unsaturated ketone with 2-cyanothioacetamide and subsequent reaction with ethyl 2-chloroacetate were performed according to the methods described in Pharmazie 44:639–640 (1989).

Yield: 65 mg. MS-ESI: [M+H]$^+$=375.0. TLC: R$_f$=0.6, silica gel, dichloromethane.

Example 87

Ethyl 3-Amino-6-naphthyl-4-phenyl-thieno[2,3-b]pyridine-2-carboxylate

Aldol condensation of 2-acetonaphthone (1.70 g) and benzaldehyde (1.12 ml), cyclisation of the α,β-unsaturated ketone with 2-cyanothioacetamide and subsequent reaction with ethyl 2-chloroacetate were performed according to the methods described in example 86.

Yield: 1.05 g. MS-ESI: [M+H]$^+$=425.2. TLC: R$_f$=0.75, silica gel, dichloromethane.

Example 88

Ethyl 3-Amino-4-phenyl-6-(2-thienyl)-thieno[2,3-b]pyridine-2-carboxylate

Aldol condensation of 2-acetylthiophene (1.08 ml) and benzaldehyde (1.12 ml), cyclisation of the α,β-unsaturated ketone with 2-cyanothioacetamide and subsequent reaction with ethyl 2-chloroacetate were performed according to the methods described in example 86.

Yield: 767 mg. MS-ESI: [M+H]$^+$=381.2. TLC: R$_f$=0.70, silica gel, dichloromethane.

Example 89

Ethyl 3-Amino-6-naphthyl-4-(2-thienyl)-thieno[2,3-b]pyridine-2-carboxylate

Aldol condensation of 2-acetonaphthone (1.70 g) and 2-thiophenecarboxaldehyde (1.03 ml), cyclisation of the α,β-unsaturated ketone with 2-cyanothioacetamide and subsequent reaction with ethyl 2-chloroacetate were performed according to the methods described in example 86.

Yield: 1.58 g. MS-ESI: [M+H]$^+$=431.2. TLC: R$_f$=0.75, silica gel, dichloromethane.

Example 90

Ethyl 3-Amino-6-phenyl-4-(2-thienyl)-thieno[2,3-b]pyridine-2-carboxylate

Aldol condensation of acetophenone (1.17 ml) and 2-thiophenecarboxaldehyde (1.03 ml), cyclisation of the α,β-unsaturated ketone with 2-cyanothioacetamide and subsequent reaction with ethyl 2-chloroacetate were performed according to the methods described in example 86.

Yield: 1.04 g. MS-ESI: [M+H]$^+$=381.2. TLC: R$_f$=0.70, silica gel, dichloromethane.

Example 91

Ethyl 3-Amino-4-(2-furyl)-4-(2-thienyl)-thieno[2,3-b]pyridine-2-carboxylate

Aldol condensation of 2-furaldehyde (1.01 g) and 2-thiophenecarboxaldehyde (1.03 ml), cyclisation of the α,β-unsaturated ketone with 2-cyanothioacetamide and subsequent reaction with ethyl 2-chloroacetate were performed according to the methods described in example 86.

Yield: 443 mg. MS-ESI: [M+H]$^+$=371.2. TLC: R$_f$=0.55, silica gel, dichloromethane.

Example 92

Ethyl 3-Amino-4,6-di-(2-thienyl)-thieno[2,3-b]pyridine-2-carboxylate

Aldol condensation of 2-acetylthiophene (1.08 ml) and 2-thiophenecarboxaldehyde (1.03 ml), cyclisation of the α,β-unsaturated ketone with 2-cyanothioacetamide and subsequent reaction with ethyl 2-chloroacetate were performed according to the methods described in example 86.

Yield: 1.04 g. MS-ESI: $[M+H]^+$=387.0. TLC: $R_f$=0.76, silica gel, dichloromethane.

Example 93

Ethyl 3-Amino-4-(3-methoxyphenyl)-6-phenyl-thieno[2,3-b]pyridine-2-carboxylate

Aldol condensation of acetophenone (1.17 ml) and 3-methoxybenzaldehyde (1.4 ml), cyclisation of the α,β-unsaturated ketone with 2-cyanothioacetamide and subsequent reaction with ethyl 2-chloroacetate were performed according to the methods described in example 86.

Yield: 164 mg. MS-ESI: $[M+H]^+$=405.2. TLC: $R_f$=0.65, silica gel, dichloromethane.

Example 94

3-Amino-2-benzoyl-4,6-diphenyl-thieno[2,3-b]pyridine

Aldol condensation of acetophenone (2.33 ml) and benzaldehyde (2.24 ml), cyclisation of the α,β-unsaturated ketone with 2-cyanothioacetamide and subsequent reaction with 2-chloroacetophenone were performed according to the methods described in example 86.

Yield: 57 mg. MS-ESI: $[M+H]^+$=407.4. TLC: $R_f$=0.65, silica gel, dichloromethane.

Example 95

3-Amino-2-benzoyl-6-napthyl-4-phenyl-thieno[2,3-b]pyridine

Aldol condensation of 2-acetonaphthone (1.70 g) and benzaldehyde (1.12 ml), cyclisation of the α,β-unsaturated ketone with 2-cyanothioacetamide and subsequent reaction with 2-chloroacetophenone were performed according to the methods described in example 86.

Yield: 50 mg. MS-ESI: $[M+H]^+$=457.2. TLC: $R_f$=0.69, silica gel, dichloromethane.

Example 96

3-Amino-2-benzoyl-4-phenyl-6-(2-thienyl)-thieno[2,3-b]pyridine

Aldol condensation of 2-acetylthiophene (1.08 ml) and benzaldehyde (1.12 ml), cyclisation of the α,β-unsaturated ketone with 2-cyanothioacetamide and subsequent reaction with 2-chloroacetophenone were performed according to the methods described in example 86.

Yield: 57 mg. MS-ESI: $[M+H]^+$=413.2. TLC: $R_f$=0.69, silica gel, dichloromethane.

Example 97

3-Amino-2-benzoyl-6-naphthyl-4-(2-thienyl)-thieno[2,3-b]pyridine

Aldol condensation of 2-acetonaphthone (1.70 g) and 2-thiophenecarboxaldehyde (1.03 ml), cyclisation of the α,β-unsaturated ketone with 2-cyanothioacetamide and subsequent reaction with 2-chloroacetophenone were performed according to the methods described in example 86.

Yield: 66 mg. MS-ESI: $[M+H]^+$=463.0. TLC: $R_f$=0.67, silica gel, dichloromethane.

Example 98

3-Amino-2-benzoyl-6-phenyl-4-(2-thienyl)-thieno[2,3-b]pyridine

Aldol condensation of acetophenone (1.17 ml) and 2-thiophenecarboxaldehyde (1.03 ml), cyclisation of the α,β-unsaturated ketone with 2-cyanothioacetamide and subsequent reaction with 2-chloroacetophenone were performed according to the methods described in example 86.

Yield: 67 mg. MS-ESI: $[M+H]^+$=413.2. TLC: $R_f$=0.71, silica gel, dichloromethane.

Example 99

3-Amino-2-benzoyl-6-(2-furyl)-4-(2-thienyl)-thieno[2,3-b]pyridine

Aldol condensation of 2-acetylfuran (1.01 g) and 2-thiophenecarboxaldehyde (1.03 ml), cyclisation of the α,β-unsaturated ketone with 2-cyanothioacetamide and subsequent reaction with 2-chloroacetophenone were performed according to the methods described in example 86.

Yield: 65 mg. MS-ESI: $[M+H]^+$=403.2. TLC: $R_f$=0.65, silica gel, dichloromethane.

Example 100

3-Amino-2-benzoyl-4,6-di-(2-thienyl)-thieno[2,3-b]pyridine

Aldol condensation of 2-acetylthiophene (1.08 ml) and 2-thiophenecarboxaldehyde (1.03 ml), cyclisation of the α,β-unsaturated ketone with 2-cyanothioacetamide and subsequent reaction with 2-chloroacetophenone were performed according to the methods described in example 86.

Yield: 67 mg. MS-ESI: $[M+H]^+$=419.0. TLC: $R_f$=0.57, silica gel, dichloromethane.

Example 101

3-Amino-2-benzoyl-4-(3-methoxyphenyl)-6-phenyl-thieno[2,3-b]pyridine

Aldol condensation of acetophenone (1.17 ml) and 3-methoxybenzaldehyde (1.4 ml), cyclisation of the α,β-unsaturated ketone with 2-cyanothioacetamide and subsequent reaction with 2-chlorocetophenone were performed according to the methods described in example 86.

Yield: 31 mg. MS-ESI: $[M+H]^+$=437.2. TLC: $R_f$=0.57, silica gel, dichloromethane.

Example 102

Isopropyl 3-Amino-4,6-diphenyl-thieno[2,3-b]pyridine-2-carboxamide (a). 3-Amino-4,6-diphenyl-thieno[2,3-b]pyridine-2-carboxylic Acid Lithium hydroxide (59 mg) was added to a stirred solution of 53 mg ethyl 3-amino-4,2-diphenyl-thieno[2,3-b]pyridine-2-carboxylate (see example 86) in dioxane/water=9/1 (v/v) and the mixture was heated at 80° C. for 72 h. The reaction mixture was cooled to r.t. and acidified to pH2. The crystals were collected by filtration and dried in vacuo.

Yield: 33 mg. MS-ESI: [M+H]⁺=47.2. TLC: $R_f$=0.05, silica gel, dichloromethane/methanol 97/3 v/v.

(b). Isopropyl 3-Amino-4,6-diphenyl-thieno[2,3-b]pyridine-2-carboxamide

To a stirred solution of 3-amino-4,6-diphenyl-thieno[2,3-b]pyridine-2carboxylic acid (33 mg) in dichloromethane was added N,N-diisopropylethylamine (36 µl), isopropylamine (12 µl) and O-(benzotriazol-1-yl)-N,N,N',N'-tetramethyluronium tetrafluoroborate (33 mg). After 16 h the solvent was evaporated and the residue was chromatographed on silicagel in dichloromethane as eluent.

Yield: 21 mg. MS-ESI: [M+H]⁺=388.2. TLC: $R_f$=0.6, silica gel, dichloromethane/methanol 97/3 v/v.

Example 103

Isopropyl 3-Amino-6-naphthyl-4-phenyl-thieno[2,3-b]pyridine-2-carboxamide

Ethyl 3-amino-6-naphthyl-4-phenyl-thieno[2,3-b]pyridine-2-carboxylate (see example 87) was first hydrolyzed to the corresponding acid (50 mg) and subsequently reacted with isopropylamine (16 µl) to the corresponding amide using the methods described in example 102.

Yield: 17 mg. MS-ESI: [M+H]⁺=438.2. TLC: $R_f$=0.6, silica gel, dichloromethane/methanol 97/3 v/v.

Example 104

Isopropyl 3-Amino-4-phenyl-6-(2-thienyl)-thieno[2,3-b]pyridine-2-carboxamide

Ethyl 3-amino-4-phenyl-6-(2-thienyl)-thieno[2,3-b]pyridine-2-carboxylate (see example 88) was first hydrolyzed to the corresponding acid (50 mg) and subsequently reacted with isopropylamine (18 µl) to the corresponding amide using the methods described in example 102.

Yield: 6 mg. MS-ESI: [M+H]⁺=394.2. TLC: $R_f$=0.6, silica gel, dichloromethane/methanol 97/3 v/v.

Example 105

Isopropyl 3-amino-6-naphthyl-4-(2-thienyl)-thieno[2,3-b]pyridine-2-carboxamide

Ethyl 3-amino-6-naphthyl-4-(2-thienyl)-thieno[2,3-b]pyridine-2-carboxylate (see example 89) was first hydrolyzed to the corresponding acid (50 mg) and subsequently reacted with isopropylamine (16 µl) to the corresponding amide using the methods described in example 102.

Yield: 16 mg. MS-ESI: [M+H]⁺=444.2. TLC: $R_f$=0.6, silica gel, dichloromethane/methanol 97/3 v/v.

Example 106

Isopropyl 3-Amino-6-phenyl-4-(2-thienyl)-thieno[2,3-b]pyridine-2-carboxamide

Ethyl 3-amino-6-phenyl-4-(2-thienyl)-thieno[2,3-b]pyridine-2-carboxylate (see example 90) was first hydrolyzed to the corresponding acid (50 mg) and subsequently reacted with isopropylamine (18 µl) to the corresponding amide using the methods described in example 102.

Yield: 16 mg. MS-ESI: [M+H]⁺=394.2. TLC: $R_f$=0.6, silica gel, dichloromethane/methanol 97/3 v/v.

Example 107

Isopropyl 3-Amino-6-(2-furyl)-4-(2-thienyl)-thieno[2,3-b]pyridine-2-carboxamide

Ethyl 3-Amino-6-(2-furyl)-4-(2-thienyl)-thieno[2,3-b]pyridine-2-carboxylate (see example 91) was first hydrolyzed to the corresponding acid (50 mg) and subsequently reacted with isopropylamine (18 µl) to the corresponding amide using the methods described in example 102.

Yield: 7 mg. MS-ESI: [M+H]⁺=384.0. TLC: $R_f$=0.6, silica gel, dichloromethane/methanol 97/3 v/v.

Example 108

Isopropyl 3-Amino-4,6-di-(2-thienyl)-thieno[2,3-b]pyridine-2-carboxamide

Ethyl 3-amino-4,6-di-(2-thienyl)-thieno[2,3-b]pyridine-2-carboxylate (see example 92) was first hydrolyzed to the corresponding acid (50 mg) and subsequently reacted with isopropylamine (18 µl) to the corresponding amide using the methods described in example 102.

Yield: 35 mg. MS-ESI: [M+H]⁺=400.2. TLC: $R_f$=0.6, silica gel, dichloromethane/methanol 97/3 v/v.

Example 109

Isopropyl 3-Amino-4-(3-methoxyphenyl)-6-phenyl-thieno[2,3-b]pyridine-2-carboxamide Ethyl 3-amino-4-(3-methoxyphenyl)-6-phenyl-thieno[2,3-b]pyridine-2-carboxylate (see example 93) was first hydrolyzed to the corresponding acid (50 mg) and subsequently reacted with isopropylamine (17 µl) to the corresponding amide using the methods described in example 102.

Yield: 28 mg. MS-ESI: [M+H]⁺=418.2. TLC: $R_f$=0.6, silica gel, dichloromethane/methanol 97/3 v/v.

Example 110 tert-Butyl 3-Amino-6-methylthio-4-(3-methoxyphenyl)-thieno[2,3-b]pyridine-2-carboxamide (a). 1,1-Dicanyo-2-methyl-2-(3-methoxyphenyl)-ethene A solution of 3'-methoxy-acetophenone (3.46 g) and malonitrile (6.89 ml) in benzene (40 ml) was treated with AcOH (2.30 ml) and ammonium acetate (1.50 g) and the reaction mixture was heated under azeotropic destination in a Dean-Stark apparatus. After 5 h, the reaction mixture was cooled to ambient temperature, diluted with EtOAc, washed with water and brine, dried (MgSO₄) and concentrated in vacuo. The residue was purified by flash silicagel chromatography using EtOAc/heptane (3/7 v/v) as eluent.

Yield: 6.4 g. MS-ESI: [M+H]⁺=199.2. TLC: $R_f$=0.6, silica gel, EtOAc/heptane 2/3 v/v.

(b). 1,1-di-(Methylthio)-3-(3-methoxyphenyl)-4,4-dicyano-butadiene 1,1-Dicyano-2-methyl-2-(3-methoxyphenyl)ethene (example 110a, 6.4 g), carbon disulfide (3.85 ml) and methyl iodide (9.9 ml) were added to a previously prepared suspension of sodium hydride (60% dispersion in mineral oil, 1.60 g) in DMF (200 ml). After 7 h, the reaction mixture was concentrated under reduced pressure, redissolved in EtOAc, washed with water and brine, dried (MgSO₄) and concentrated in vacuo. The residue was purified using silica gel chromatography (eluent: EtOAc/heptane 3/7 v/v).

Yield: 3.92 g. MS-ESI: [M+H]⁺=303.1. TLC: $R_f$=0.5, silica gel, EtOAc/heptane 2/3 v/v.

(c). 2-Methylthio-4-(3-methoxyphenyl)-5-cyano-pyridin-6-one

A solution of 1,1-di-(methylthio)-3,3-methoxyphenyl)-4,4-dicyano-butadiene (example 110b, 3.92 g) in EtOH (50 ml) was treated with 48% aq. HBr (39 ml) and the solution was heated under reflux for 3 h. After cooling of the reaction mixture in an ice bath (0° C.), the precipitate was filtered off, washed with water and dried under vacuum.

Yield: 2.4 g. MS-ESI: [M+H]$^+$=273.2. TLC: R$_f$=0.47, silica gel, CH$_2$Cl$_2$/MeOH 9/1 v/v.

(d). tert-Butyl 3-Amino-6-methylthio-4-(3-methoxyphenyl)-thieno[2,3-b]pyridine-2-carboxamide Treatment of 2-methylthio-3-methoxyphenyl)-5-cyanopyridinone (2,4 g, example 110c) with POCl$_3$ and subsequent reaction with ethyl 2-mercaptoacetate were performed according to the methods described in example 1. The resulting derivative ethyl 3-amino-4-(3-methoxyphenyl)-6-methylthio-thieno[2,3-b]pyrimidine-2-carboxylate (2.6 g) was first hydrolyzed to the corresponding acid (2.2 g) using the method described in example 34 and subsequently reacted with tert-butyl amine (2 ml) to provide the corresponding amide according to example 50. The title compound was purified by chromatography on silicagel in heptane/EtOAc=3/1 (v/v) as eluent.

Yield: 2.11 g. MS-ESI: [M+H]$^+$=402.3. TLC: R$_f$=0.37, silica gel, heptane/EtOAc=3/2 (v/v).

Example 111 tert-Butyl 5-Amino-2-methylthio-4-(N-benzoyl-3-aminophenyl)-thieno[2,3-d]pyrimidine-6-carboxamide (a). Ethyl 5-Amino-2-methylthio-4-(3-nitrophenyl)thieno[2,3-d]pyrimidine-6-carboxamide Cyclization of S-methylisothiourea sulfate (700 mg), 3-nitrobenaaldehyde (750 mg) and ethyl cyanoacetate (560 µl), treatment of the product with POCl$_3$ and subsequent reaction with ethyl 2-mercaptoacetate were performed according to the methods described in example 1. The pure title compound was obtained after chromatography on silicagel in heptane/EtOAc=3/2 (v/v) as eluent.

Yield: 780 mg. MS-ESI: [M+H]$^+$=391.3. TLC: R$_f$=0.35, silica gel, heptane/EtOAc=3/2 (v/v).

(b). tert-Butyl 5-Amino-2-methylthio-4-(3-aminophenyl)-thieno[2,3-d]pyrimidine-6-carboxamide Ethyl 5-amino-2-methylthio-4-(3-nitrophenyl)-thieno[2,3-b]pyrimidine-6-carboxamide (example 111a, 780 mg) was dissolved in 10 ml dioxane. Subsequently, 10 ml EtOH and tin(II)chloride (1.1 g) were added and the reaction mixture was stirred overnight at 90° C. After concentration of the reaction mixture in vacuo, the residue was redissolved in EtOAc (50 ml) and washed with 10 ml 4 M NaOH, dried (MgSO$_4$) and concentrated under reduced pressure. The ethyl ester in the resulting derivative ethyl 5-amino-2-methylthio-4-(3-aminophenyl)-thieno[2,3-d]pyrimidine-6-carboxamide (558 mg) was saponified to the corresponding acid (430 mg) using the method described in example 34 and subsequently reacted with tert-butyl amine (200 µl) to form the corresponding tert-butyl amide (according to example 50). The title compound was purified by chromatography on silicagel in heptane/EtOAc=3/1 (v/v) as eluent.

Yield: 391 mg. MS-ESI: [M+H]$^+$=388.0. TLC: R$_f$=0.43, silica gel, heptane/EtOAc=312 (v/v).

(c) tert-Butyl 5-Amino-2-methylthio-4-(N-benzoyl-3-aminophenyl)-thieno[2,3-d]pyrimidine-6-carboxamide tert-Butyl 5-amino-2-methylthio-4-(3-aminophenyl)-thieno[2,3-d]pyrimidine-6-carboxamide (example 111b, 391 mg) was dissolved in 10 ml CH$_2$Cl$_2$. Subsequently, N,N-diisopropylethylamine (600 µl) and benzoyl chloride (210 mg) were added and the reaction mixture was stirred for 2 h. The reaction mixture mixture was diluted with CH$_2$Cl$_2$ (50 ml) and washed with sat. aq. NaHCO. The organic layer was dried (MgSO$_4$) and concentrated under reduced pressure. The title compound was purified by chromatography on silicagel in heptane/EtOAc=3/1 (v/v) as eluent.

Yield: 348 mg. MS-ESI: [M+H]$^+$=492.1. TLC: R$_f$=0.50, silica gel, heptane/EtOAc=3/2 (v/v).

Example 112 tert-Butyl 5-Amino-2-methylthio-4-(3-methoxyphenyl)-thieno[2,3-d]pyrimidine-6-carboxamide Ethyl 5-amino-4-(3-methoxyphenyl)-2-methylthio-thieno[2,3-d]pyrimidine-6-carboxamide (see example 1, 400 mg) was first hydrolyzed to the corresponding acid (340 mg) using the method described in example 34 and subsequently reacted with tert-butyl amine (150 µl) to give the corresponding amide according to example 50. The title compound was purified by chromatography on silicagel in heptane/EtOAc=3/1 (v/v) as eluent.

Yield: 310 mg. MS-ESI: [M+H]$^+$=403.0. TLC: R$_f$=0.32, silica gel, heptane/EtOAc=3/2 (v/v).

Example 113

N-Methyl-N-isopropyl 5-Amino-2-methylthio-4-(3-methoxyphenyl)-thieno[2,3-d]pyrimidine-6-carboxamide Ethyl 5-amino-4-(3-methoxyphenyl)-2-methylthio-thieno[2,3-d]pyrimidine-6-carboxamide (see example 1) was first hydrolyzed to the corresponding acid (340 mg) using the method described in example 34 and subsequently reacted with N-methyl-N-isopropyl amine (150 µl) to furnish the corresponding amide according to example 50. The title compound was purified by chromatography on silicagel in heptane/EtOAc 3/1 (v/v) as eluent.

Yield: 271 mg. MS-ESI: [M+H]$^+$=404.0. TLC: R$_f$=0.34, silica gel, heptane/EtOAc=3/2 (v/v).

Example 114 tert-Butyl 5-Amino-2-ethoxy-4-(3-methoxyphenyl)-thieno[2,3-d]pyrimidine-6-carboxamide tert-Butyl 5-amino-2-methylthio-4-(3-methoxyphenyl)-thieno[2,3-d]pyrimidine-6-carboxamide (see example 112, 1.1 g) was dissolved in trifluoroacetic acid (20 ml) and 3-chloroperbenzoic acid (mCPBA, 1.23 g) was added. After stirring for 2 h, the reaction mixture was concentrated in vacuo, redissolved in CH$_2$Cl$_2$ (50 ml), washed with aq. sat. NaHCO$_3$, dried (MgSO$_4$) and concentrated under reduced pressure. The residue, containing the corresponding 2-methyl sulfoxide, was subsequently dissolved in EtOH (10 ml) and KOtBu (1 g) was added. After heating under reflux overnight, the reaction mixture was acidified with 1 M HCl, concentrated in vacuo, redissolved in CH$_2$Cl$_2$ (50 ml), washed with aq. sat. NaHCO$_3$, dried (MgSO$_4$) and concentrated under reduced pressure. Purification of the thus obtained oil was effected by chromatography on silicagel using heptane/EtOAc=3/1 (v/v) as eluent.

Yield: 356 mg. MS-ESI: [M+H]=401.6. TLC: R$_f$=0.50, silica gel, heptane/EtOAc=3/2 (v/v).

Example 115

5-Amino-2-(2-thienyl)-4-(3-methoxyphenyl)-6-(N-morpholinocarbonyl)thieno[2,3-d]pyrimidine Ethyl 5-amino-4-(3-methoxyphenyl)-2,2-thienyl)-thieno[2,3-d]pyrimidine-6-carboxylate (561 mg, see example 27)

was first hydrolyzed to the corresponding acid (464 mg) using the method described in example 34 and subsequently reacted with morpholine (300 μl) to afford the corresponding amide according to example 50. The title compound was chromatographed on silicagel in heptane/EtOAc=3/2 (v/v) as eluent.

Yield: 457 mg. MS-ESI: [M+H]$^+$=453.2. TLC: R$_f$=0.16, silica gel, heptane/EtOAc=3/2 (v/v).

Example 116 tert-Butyl 5-Amino-2-methylthio-4-(N-(2-(tert-butylamino)acetyl)-3-aminophenyl)-thieno[2,3-d]pyrimidine-6-carboxamide tert-Butyl 5-amino-2-methylthio-4-(3-aminophenyl)-thieno[2,3-d]pyrimidine-6-carboxamide (example 111b, 195 mg) was dissolved in 5 ml CH$_2$Cl$_2$. Subsequently, N,N-diisopropylethylamine (300 μl) and bromoacetyl chloride (120 mg) were added and the reaction mixture was stirred for 2 h The reaction mixture mixture was diluted with CH$_2$Cl$_2$ (20 ml) and washed with sat. aq. NaHCO$_3$. The organic layer was then treated with tert-butyl amine (2 ml). After standing overnight, the reaction mixture was washed again with sat. aq. NaHCO$_3$, dried (MgSO4) and concentrated in vacuo. Purification of the residue was accomplished using silica chromatography (eluent: CH$_2$Cl$_2$/MeOH=1/0 to 9/1 (v/v)).

Yield: 155 mg. MS-ESI: [M+H]$^+$=501.2. TLC: R$_f$=0.64, silica gel, CH$_2$Cl$_2$/MeOH=9/1 (v/v).

Example 117 tert-Butyl 5-Amino-2-methylthio-4-(3-(3-(3-pyridyl)-propoxy)phenyl)-thieno[2,3-d]pyrimidine-6-carboxamide tert-Butyl 5-amino-2-methylthio-4-(3-methoxyphenyl)-thieno[2,3-d]pyrimidine-6-carboxamide (400 mg, example 112) was dissolved in cooled (0° C.) CH$_2$Cl$_2$ (10 ml) and BBr$_3$ (300 μl) was added dropwise. After stirring overnight at room temperature, the reaction mixture was diluted with CH$_2$Cl$_2$ (50 ml) and washed with sat aq. NaHCO$_3$. The organic layer was dried (MgSO$_4$) and concentrated to near dryness. The remaining oil was added dropwise to a flask with stirred toluene (50 ml). The thus obtained precipitate (360 mg), containing tert-butyl 5-amino-2-methylthio-4-(3-hydroxyphenyl)-thieno[2,3-d]pyrimidine-6-carboxamide was filtered off and dried in vacuo. The latter derivative was dissolved in THF (10 ml) and PPh$_3$ (600 mg), 3-(3-pyridyl)-propanol (270 mg) and azodicarbonyldipiperidine (ADDP, 600 mg) were added. After stirring overnight, the reaction mixture was diluted with CH$_2$Cl$_2$ (50 ml), washed with sat. aq. NaHCO$_3$, dried (MgSO$_4$) and purified by silicagel chromatography (eluent: CH$_2$Cl$_2$/MeOH=1/0 to 95/5 (v/v)).

Yield: 271 mg. MS-ESI: [M+H]$^+$=508.2. TLC: R$_f$=0.56, silica gel, CH$_2$Cl$_2$/MeOH=96/4 (v/v).

Example 118

In Vitro Test for LH Bioactivity in Mouse Leydig Cells

In male mice, the luteinising hormone (LH) induces testosterone production in testicular Leydig cells. This activity is also displayed by human chorionic gonadotrophin (hCG) which binds to the same target cell receptor as LH. The in vitro Leydig cell assay (van Damme et al, 1974; modified by Mannaerts et al, 1987) is used to determine the LH bioactivity of compounds that bind to the Leydig cell LH receptor which in turn causes testosterone production.

For this assay, Leydig cells are isolated from the testes of mature, 9 to 13 weeks old, mice (strain: HSD/Cpb: S E, Harlan, The Netherlands). Therefore, mice are killed and the testes are quickly removed and decapsulated. Each testis is transferred to a separate well of a tissue culture plate containing 0.75 ml culture medium per well. The contents of each well are passed through a 30 cm glass tube (inside diameter 2.5 mm, narrowed to 1.2 mm at 4 places in the middle). The suspension obtained is filtered through a 30 μm nylon mesh and the filtrate is pre-incubated in a 50 ml plastic tube for 30 min. at 37° C. in an incubator in a water-saturated atmosphere of 95% air/5% CO2. Following preincubation the tube is centrifuged at 1600 N/kg for 5 min and the supernatant is decanted. The resulting pellet is resuspended in culture medium (0.5 mg original testis/ml) and the suspension is kept homogeneous by stirring it very slowly on a magnetic stirrer.

This Leydig cell suspension (100 μl) is added to the wells of a micotiter plate containing 50 μl reference compound, test compound or vehicle (culture medium) per well. As a to reference, LH or hCG in-house standards are used which are calibrated against International Reference preparations of human LH or hCG provided by the National Institute for Biological Standards and Controls (NIBSC, London, UK). Test and reference compounds are dissolved, diluted and assayed in the same culture medium. The plates containing reference and test compounds are incubated for 4 h at 37° C. in an incubator in a water-saturated atmosphere of 95% air/5% CO2. Following incubation, plates are sealed and stored at −20° C. until testosterone measurement.

Prior to testosterone measurement, the contents of the microtiter plates are thawed at room temperature and the plates are centriged at 150 N/kg for 5 min. An aliquot of 30 μl supernatant of each well is diluted with culture medium (60×) to obtain a suitable dilution for testosterone measurement. Aliquots (12.5 μl) of each diluted test sample are then assayed using a direct testosterone RIA-kit. Results are indicated in Table 1.

Example 119

In Vivo Ovulation Induction Assay for LH Bioactivity in Immature Female Mice

In female immature mice which are stimulated with follicle stimulating hormone (FSH), ovulation can be induced by luteininzing hormone (LH) or by human chorionic gonadotrophin (hCG) which binds to the same LH-receptor on the Graafian follicles. Binding to the LH-receptor initiates a biochemical cascade, which eventually results in follicular rupture and extrusion of a mature oocyte. To measure the in vivo activity of LH-agonistic compounds, inunature 20 days old mice (B6D2F1 stain, Broekman Institute, the Netherlands) are primed with unary FSH (Humegon; 12.5 IU/l, 0.1 ml s.c.) to initiate folliculogenesis. Forty-eight hours after FSH treatment test compound, reference compound or vehicle (10% cremophor solution) are administered to the animals. Test compounds (50 mg/kg in 0.1 ml) and vehicle (0.1 ml) are administered p.o., reference compounds (500 IU/kg hCG in 0.1 ml) are injected s.c. As a reference, hCG in-house standards are used which are calibrated against International Reference preparations of human hCG provided by the National Institute for Biological Standards and Controls (NMSC, London, UK). Twenty-four hours after administration of test compound, reference compound or vehicle, animals are killed by cervical dislocation. The oviducts are dissected and collected in 0.9% NaCl. Next, the oviducts are placed between two glass plates and examined for the presence or absence of ovulated ova under a microscope. The number of ovulated ova present in the oviducts is indicative for in vivo LH-bioactivity. Results are given in Table 1.

TABLE 1

| Compound | Leydig cell assay ($EC_{50}$) | Mouse in vivo ovulation induction (% ovulating animals) |
| --- | --- | --- |
| Control p.o. (cremophor 10%) | — | 0% |
| Urinary hCG s.c. (20 IU/kg) | — | 100% |
| tert-Butyl 5-amino-2-methylthio-4-(N-benzoyl-3-aminophenyl)-thieno[2,3-d]pyrimidine-6-carboxamide (50 mg/kg p.o.) | $2.8 \ 10^{-7}$ M | 40% |
| tert-Butyl 5-amino-2-methylthio-4-(3-methoxyphenyl)-thieno[2,3-d]pyrimidine-6-carboxamide (50 mg/kg p.o.) | $4.3 \ 10^{-7}$ M | 40% |
| N-Methyl-N-isopropyl 5-amino-2-methylthio-4-(3-methoxyphenyl)-thieno[2,3-d]pyrimidine-6-carboxamide (50 mg/kg p.o.) | $8.7 \ 10^{-7}$ M | 50% |
| tert-Butyl 5-amino-2-ethoxy-4-(3-methoxyphenyl)-thieno[2,3-d]pyrimidine-6-carboxamide (50 mg/kg p.o.) | $1.9 \ 10^{-6}$ M | 30% |
| 5-Amino-2-(2-thienyl)-4-(3-methoxyphenyl)-6-(N-morpholinocarbonyl) thieno[2,3-d]pyrimidine (50 mg/kg p.o.) | $3.1 \ 10^{-6}$ M | 20% |
| tert-Butyl 5-amino-2-methylthio-4-(N-(2-(tert-butylamino)-acetyl)-3-aminophenyl)-thieno[2,3-d]pyrimidine-6-carboxamide (50 mg/kg p.o.) | $3.2 \ 10^{-7}$ M | 13% |
| tert-Butyl 5-amino-2-methylthio-4-(3-(3-(3-pyridyl)-propoxy)-phenyl)-thieno[2,3-d]pyrimidine-6-carboxamide (50 mg/kg p.o.) | $1.8 \ 10^{-6}$ M | 40% |

What is claimed is:

1. A method for controlling fertility, comprising:

administering an effective amount of a bicyclic heteroaromatic compound of Forumla I,

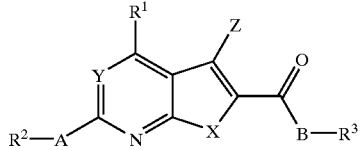

Formula I wherein $R^1$ is $NR^5R^6$, $OR^5$, $SR^5$ or $R^7$;

$R^5$ and $R^6$ are independently selected from H, (1–8C) alkyl, (2–8C)alkenyl, (2–8C)alkynyl, (3–8C) cycloalkyl, (2–7C)heterocycloalkyl, alkyl(1–8C) carbonyl, (6–14C)arylcarbonyl, (6–14C)aryl and (4–13C)heteroaryl, or $R^5$ and $R^6$ together are joined in a (2–7C)heterocycloalkyl ring;

$R^7$ is (3–8C)cycloalkyl, (2–13C)heteroaryl;

$R^2$ is (1–8C)alkyl, (2–8C)alkeny, (16–14C)aryl or (4–13C)heteroaryl, the (6–14C)aryl and (4–13C heteroaryl optionally substituted with one or more substituents selected from (1–8C)alkyl, (1–8C)alkylthio, (1–8C) (di)alkylamino, (1–8C)alkoxy, (2–8C)alkenyl, or (2 –8C)alkynyl;

$R^3$ is (1–8C)alkyl, (2–8C)alkenyl, (2–8C)alkynyl, (3–8C) cycloalkyl, (2–7C)heterocycloaklyl, (6–14C)aryl, or (4–13C)heteroaryl, the (5–14C)aryl and (4–13C) heteroaryl optionally sustituted with one or more substituents selected from (1–8C)alkyl, (1–8C) (di) alkylamino and (1–8C);

X is S or O;

Y is N;

Z is $NH_2$ or OH;

A is S, N(H), N($R^9$), O or a bond;

$R^9$ is selected from the same group as described for $R^2$;

B is N(H), O or a bond;

or a salt thereof to a subject.

2. The method according to claim 1, wherein X is S and Z is $NH_2$ in the bicyclic heteroaromatic compound.

3. The method according to claim 1, wherein X is S, Z is $NH_2$ and $R^1$ is (6–14C)aryl or (4–13C)heteroaryl in the bicyclic heteroaromatic compound.

4. The method according to claim 1, wherein B is N(H) or O in the bicyclic heteroaromatic compound.

5. The method according to claim 4, wherein B is N(H) in the bicyclic heteroaromatic compound.

6. The method according to claim 1, wherein $R^3$ is isoproply or tert-butyl in the bicyclic heteroaromatic compound.

* * * * *